(12) United States Patent
Asfora et al.

(10) Patent No.: US 10,603,054 B2
(45) Date of Patent: Mar. 31, 2020

(54) PARALLEL GUIDE FOR SURGICAL IMPLANTS

(71) Applicant: SICAGE LLC, Sioux Falls, SD (US)

(72) Inventors: Wilson Theophilo Asfora, Sioux Falls, SD (US); Daniel S. Savage, Brecksville, OH (US)

(73) Assignee: SICAGE LLC, Souix Falls, SD (US)

( * ) Notice: Subject to any disclaimer, the term of this patent is extended or adjusted under 35 U.S.C. 154(b) by 213 days.

(21) Appl. No.: 15/799,419

(22) Filed: Oct. 31, 2017

(65) Prior Publication Data
US 2019/0125370 A1    May 2, 2019

(51) Int. Cl.
*A61B 17/17*    (2006.01)

(52) U.S. Cl.
CPC .................. *A61B 17/1757* (2013.01)

(58) Field of Classification Search
CPC ... A61B 17/17; A61B 17/1703; A61B 17/171; A61B 17/1714; A61B 17/1717;
(Continued)

(56) References Cited

U.S. PATENT DOCUMENTS

| 4,486,689 A | 12/1984 | Davis |
| 4,563,727 A | 1/1986 | Curiel |

(Continued)

FOREIGN PATENT DOCUMENTS

| RU | 2489983 C1 | 8/2013 |

OTHER PUBLICATIONS

65mm Flat Semi Circle Silicone Necklace Mold PM04, no date available, online, site visited Feb. 1, 2019, retrieved from url:https://www.makememoldme.com/listing/588778232/65mm-flat-semi-circle-silicone-mold (2019).

(Continued)

*Primary Examiner* — Eric S Gibson
(74) *Attorney, Agent, or Firm* — Fox Rothschild LLP

(57) ABSTRACT

Disclosed herein is a parallel spacer for parallel spacing of a guide wire/pin during surgery. The parallel spacer includes a parallel spacer body having a top surface and a bottom surface. The parallel spacer also includes a first aperture extending through the body and defined by one or more internal walls that extends to the opening in the top surface. The aperture is sized to receive a first guide and hold the first guide in a first orientation. A second aperture extends between a second opening in the top surface and a second opening in the bottom surface. The second aperture is defined by one or more walls located within the spacer body. The one or more walls connect the second opening in the top surface to the second opening in the bottom surface. The aperture is sized to receive another guide and hold the other guide in a parallel orientation to the first orientation at a first distance from the first aperture. A third aperture extends between a third opening in the top surface and a third opening in the bottom surface. The third aperture is defined by one or more walls located within the spacer body. The one or more walls connect the third opening in the top surface to the third opening in the bottom surface. The aperture is sized to receive another guide and hold the other guide in a parallel orientation to the first orientation at a second distance from the first aperture. The parallel spacer also includes at least two spacer markings. A first spacer marking is positioned adjacent to the second aperture and a second spacer marking is positioned adjacent to the third aperture. Each of the two spacer markings mark the first distance and the second distance.

29 Claims, 17 Drawing Sheets

(58) Field of Classification Search
CPC ............ A61B 17/1721; A61B 17/1725; A61B 17/1728; A61B 17/1732; A61B 17/1739; A61B 17/1742; A61B 17/1757; A61B 17/1764; A61B 17/1767; A61B 17/1778
USPC .......................................................... 606/96
See application file for complete search history.

(56) References Cited

U.S. PATENT DOCUMENTS

| | | | |
|---|---|---|---|
| 4,917,111 A * | 4/1990 | Pennig | A61B 17/1703 606/97 |
| D326,156 S | 5/1992 | Martinez | |
| 5,144,946 A | 9/1992 | Weinberg | |
| 5,147,367 A * | 9/1992 | Ellis | A61B 17/1728 606/309 |
| D337,820 S | 7/1993 | Hooper | |
| 5,324,295 A * | 6/1994 | Shapiro | A61B 17/1714 606/86 R |
| 5,676,545 A | 10/1997 | Jones | |
| D389,639 S | 1/1998 | Priebe | |
| 5,725,581 A | 3/1998 | Branemark | |
| 5,727,958 A | 3/1998 | Chen | |
| 5,735,898 A | 4/1998 | Branemark | |
| D395,082 S | 6/1998 | Edgson | |
| D406,642 S | 3/1999 | Remes | |
| 6,135,772 A | 10/2000 | Jones | |
| 6,149,686 A | 11/2000 | Kuslich et al. | |
| 6,270,503 B1 | 8/2001 | Schmieding | |
| 6,287,343 B1 | 9/2001 | Kuslich et al. | |
| 6,342,055 B1 | 1/2002 | Eisermann | |
| 6,391,058 B1 | 5/2002 | Kuslich et al. | |
| 6,517,542 B1 | 2/2003 | Papay et al. | |
| 6,554,830 B1 | 4/2003 | Chappius | |
| 6,565,572 B2 | 5/2003 | Chappius | |
| 6,604,945 B1 | 8/2003 | Jones | |
| 6,755,835 B2 | 6/2004 | Schultheiss et al. | |
| D560,727 S | 1/2008 | Denoual | |
| 7,354,442 B2 | 4/2008 | Sasso et al. | |
| D588,211 S * | 3/2009 | Croston | D21/503 |
| D596,758 S | 7/2009 | Constable | |
| 7,575,572 B2 | 8/2009 | Sweeney | |
| 7,608,062 B2 | 10/2009 | Sweeney | |
| 7,658,879 B2 * | 2/2010 | Solar | A61B 90/11 264/278 |
| 7,717,947 B1 | 5/2010 | Wilberg et al. | |
| D626,615 S | 11/2010 | Isbrandt | |
| D629,517 S * | 12/2010 | Jauch | D24/140 |
| D634,428 S | 3/2011 | Anderson | |
| 8,062,270 B2 | 11/2011 | Sweeney et al. | |
| D667,548 S * | 9/2012 | Brannon | D24/140 |
| 8,303,602 B2 | 11/2012 | Biedermann et al. | |
| 8,382,808 B2 | 2/2013 | Wilberg et al. | |
| D678,187 S | 3/2013 | Huang | |
| D686,491 S | 7/2013 | Kuo | |
| 8,535,319 B2 * | 9/2013 | Ball | A61B 17/1778 606/86 R |
| D691,201 S | 10/2013 | Roth | |
| 8,574,273 B2 | 11/2013 | Russell et al. | |
| D705,719 S | 5/2014 | Wong | |
| D708,191 S | 7/2014 | An | |
| 8,808,337 B2 | 8/2014 | Sweeney et al. | |
| D714,765 S | 10/2014 | Goransson | |
| 8,870,836 B2 | 10/2014 | Sweeney | |
| 8,911,445 B2 * | 12/2014 | Rocci | A61B 17/1686 606/86 R |
| 8,956,369 B2 | 2/2015 | Millett et al. | |
| D736,380 S | 8/2015 | Van Dalen | |
| 9,131,970 B2 | 9/2015 | Kang | |
| 9,138,245 B2 * | 9/2015 | Mebarak | A61B 17/1728 |
| 9,173,692 B1 | 11/2015 | Kaloostian | |
| 9,198,702 B2 | 12/2015 | Biederman et al. | |
| D748,786 S | 2/2016 | Bailey | |
| 9,271,742 B2 | 3/2016 | Asfora | |
| 9,271,743 B2 | 3/2016 | Asfora | |
| 9,295,488 B2 | 3/2016 | Asfora | |
| 9,326,779 B2 | 5/2016 | Dorawa et al. | |
| 9,326,801 B2 | 5/2016 | Poulos | |
| 9,333,018 B2 | 5/2016 | Russell et al. | |
| 9,408,705 B2 | 8/2016 | Oosthuizen | |
| D767,042 S | 9/2016 | Martin | |
| 9,445,852 B2 | 9/2016 | Sweeney | |
| 9,445,909 B2 | 9/2016 | Cohen | |
| 9,504,526 B2 * | 11/2016 | Hanson | A61M 5/3287 |
| 9,526,548 B2 | 12/2016 | Asfora | |
| D778,156 S | 2/2017 | Follett | |
| 9,566,100 B2 | 2/2017 | Asfora | |
| 9,616,205 B2 | 4/2017 | Nebosky et al. | |
| 9,642,656 B2 | 5/2017 | Kotuljac et al. | |
| D790,964 S | 7/2017 | Akana | |
| D802,536 S | 11/2017 | Shang | |
| 9,826,993 B2 * | 11/2017 | Bake | A61F 2/30756 |
| 9,826,994 B2 * | 11/2017 | Eash | A61B 17/1778 |
| D804,334 S | 12/2017 | Becker | |
| 9,855,063 B2 * | 1/2018 | Feibel | A61B 17/1717 |
| 9,907,582 B1 | 3/2018 | Olea | |
| D831,479 S | 10/2018 | Lylyk | |
| 10,111,650 B2 | 10/2018 | Nel | |
| 2003/0236527 A1 * | 12/2003 | Kawakami | A61B 17/1721 606/96 |
| 2004/0049284 A1 | 3/2004 | German | |
| 2004/0049286 A1 | 3/2004 | German | |
| 2004/0230197 A1 * | 11/2004 | Tornier | A61B 17/1778 606/87 |
| 2005/0071008 A1 | 3/2005 | Kirschman | |
| 2005/0203532 A1 | 9/2005 | Ferguson | |
| 2005/0228398 A1 | 10/2005 | Rathbun | |
| 2006/0192319 A1 * | 8/2006 | Solar | A61B 90/11 264/271.1 |
| 2006/0195111 A1 | 8/2006 | Couture | |
| 2007/0106305 A1 * | 5/2007 | Kao | A61B 90/11 606/130 |
| 2007/0233123 A1 | 10/2007 | Ahmad et al. | |
| 2008/0027458 A1 * | 1/2008 | Aikins | A61B 17/1668 606/96 |
| 2008/0086144 A1 * | 4/2008 | Zander | A61B 17/17 606/96 |
| 2008/0114370 A1 * | 5/2008 | Schoenefeld | A61B 17/1721 606/96 |
| 2008/0133020 A1 | 6/2008 | Blackwell | |
| 2008/0161820 A1 * | 7/2008 | Wack | A61B 17/88 606/96 |
| 2009/0024131 A1 * | 1/2009 | Metzger | A61B 17/1764 606/88 |
| 2009/0118736 A1 * | 5/2009 | Kreuzer | A61B 17/175 606/96 |
| 2010/0137873 A1 * | 6/2010 | Grady, Jr. | A61B 17/1728 606/96 |
| 2010/0217399 A1 * | 8/2010 | Groh | A61F 2/4081 623/19.11 |
| 2011/0040303 A1 * | 2/2011 | Iannotti | A61B 17/1778 606/96 |
| 2011/0130795 A1 * | 6/2011 | Ball | A61B 17/1778 606/86 R |
| 2011/0137352 A1 | 6/2011 | Biedermann et al. | |
| 2011/0213426 A1 | 9/2011 | Yedlicka et al. | |
| 2012/0089195 A1 | 4/2012 | Yedlicka et al. | |
| 2012/0136365 A1 * | 5/2012 | Iannotti | A61B 17/1739 606/104 |
| 2012/0197261 A1 * | 8/2012 | Rocci | A61B 17/1686 606/96 |
| 2012/0253353 A1 * | 10/2012 | McBride | A61B 17/1757 606/97 |
| 2013/0065698 A1 | 3/2013 | Biedermann et al. | |
| 2013/0190570 A1 * | 7/2013 | Hirsch | A61B 17/8861 600/204 |
| 2013/0245602 A1 | 9/2013 | Sweeney | |
| 2013/0267958 A1 * | 10/2013 | Iannotti | A61B 90/06 606/87 |
| 2013/0267960 A1 | 10/2013 | Groh | |
| 2014/0012340 A1 | 1/2014 | Beck et al. | |
| 2014/0046381 A1 | 2/2014 | Asfora | |

(56) References Cited

U.S. PATENT DOCUMENTS

| | | | |
|---|---|---|---|
| 2014/0142643 A1* | 5/2014 | Bake | A61B 17/1764 606/86 R |
| 2014/0243837 A1* | 8/2014 | Mebarak | A61B 17/1728 606/96 |
| 2014/0276857 A1 | 9/2014 | Major | |
| 2014/0277188 A1 | 9/2014 | Poulos | |
| 2015/0157337 A1* | 6/2015 | Wolf | A61B 17/1728 606/96 |
| 2015/0157379 A1 | 6/2015 | Matsuzaki | |
| 2015/0230844 A1 | 8/2015 | Ellis | |
| 2015/0272597 A1* | 10/2015 | Johannaber | A61B 17/175 606/96 |
| 2015/0272646 A1 | 10/2015 | Russell | |
| 2015/0313658 A1 | 11/2015 | Kolb | |
| 2016/0000489 A1 | 1/2016 | Kaloostian | |
| 2016/0008044 A1 | 1/2016 | Sweeney | |
| 2016/0089163 A1* | 3/2016 | Eash | A61B 17/1778 606/96 |
| 2016/0143671 A1 | 5/2016 | Jiminez | |
| 2016/0143742 A1 | 5/2016 | Asfora | |
| 2016/0151100 A1 | 6/2016 | Biedermann et al. | |
| 2016/0220291 A1 | 8/2016 | Russell et al. | |
| 2016/0310188 A1 | 10/2016 | Marino et al. | |
| 2017/0181759 A1 | 6/2017 | Bouduban | |
| 2018/0072488 A1 | 3/2018 | Benoit | |
| 2018/0185038 A1* | 7/2018 | Hero | A61F 2/30756 |
| 2019/0125370 A1* | 5/2019 | Asfora | A61B 17/1757 |

OTHER PUBLICATIONS

Citrus Slice by faberdasher, Aug. 17, 2016 online, site visited Feb. 1, 2019, retrieved from url:https://www.thingiverse.com/thing:1721009 (2016).

Silicone mold 8×3.5 mm lenses 10 pcs, earliest review Nov. 27, 2016, online, site visited Feb. 1, 2019, retrieved from url:https://www.etsy.com/listing/257627215/silicone-mold-8-x-35-mm-lenses-10-pcs?ref=shop_review (2016).

International Application PCT/US018/058550, filed Oct. 31, 2018, International Search Report and Written Opinion, dated Feb. 13, 2019.

* cited by examiner

PARALLEL GUIDE FOR SURGICAL IMPLANTS

TECHNICAL FIELD

The present invention relates generally to orthopedic surgery. More specifically, techniques, devices, and systems associated with the parallel implantation of a bone screw for joint fusion are described.

BACKGROUND

Stress across joints and in particular the sacroiliac joint generally is a common cause of pain including lower back pain. Various types of sacroiliac joint stress, including sacroiliac joint disruptions (i.e., separations) and degenerative sacroiliitis (i.e., inflammation) can result from lumbar fusion, trauma, postpartum, heavy lifting, arthritis, or unknown causes. Sacroiliac joint fixation or arthrodesis is sometimes recommended for skeletally mature patients with severe, chronic sacroiliac joint pain or acute trauma in the sacroiliac joint.

Conventional solutions for stabilizing joints and relieving pain in joints typically include the insertion of an implant, such as a metal screw, rod or bar, laterally across the joint. As multiple implants may be inserted across the joint, the relative orientation between the implants needs to be controlled. Guides that utilize a sliding mechanism are known. But such guides do not provide both flexibility and the control of discrete placement of the guides used for locating implants.

SUMMARY

The summary is illustrative only and is not intended to be in any way limiting. In addition to the illustrative aspects, embodiments, and features described above, further aspects, embodiments, and features will become apparent by reference to the drawings and the following detailed description.

In accordance with various embodiments, the parallel spacer includes a parallel spacer body having a top surface and a bottom surface. The parallel spacer also includes a first aperture extending through the body and defined by one or more internal walls that extends to the opening in the top surface. The aperture is sized to receive a first guide and hold the first guide in a first orientation. A second aperture extends between a second opening in the top surface and a second opening in the bottom surface. The second aperture is defined by one or more walls located within the spacer body. The one or more walls connect the second opening in the top surface to the second opening in the bottom surface. The aperture is sized to receive another guide and hold the other guide in a parallel orientation to the first orientation at a first distance from the first aperture. A third aperture extends between a third opening in the top surface and a third opening in the bottom surface. The third aperture is defined by one or more walls located within the spacer body. The one or more walls connect the third opening in the top surface to the third opening in the bottom surface. The aperture is sized to receive another guide and hold the other guide in a parallel orientation to the first orientation at a second distance from the first aperture. The parallel spacer also includes at least two spacer markings. A first spacer marking is positioned adjacent to the second aperture and a second spacer marking is positioned adjacent to the third aperture. Each of the two spacer-markings mark the first distance and the second distance.

BRIEF DESCRIPTION OF THE DRAWINGS

The foregoing and other features of the present disclosure will become more fully apparent from the following description and appended claims, taken in conjunction with the accompanying drawings. Understanding that these drawings depict only several examples in accordance with the disclosure and are, therefore, not to be considered limiting of its scope, the disclosure will be described with additional specificity and detail through use of the accompanying drawings, in which:

DETAILED DESCRIPTION

Figure 1A:
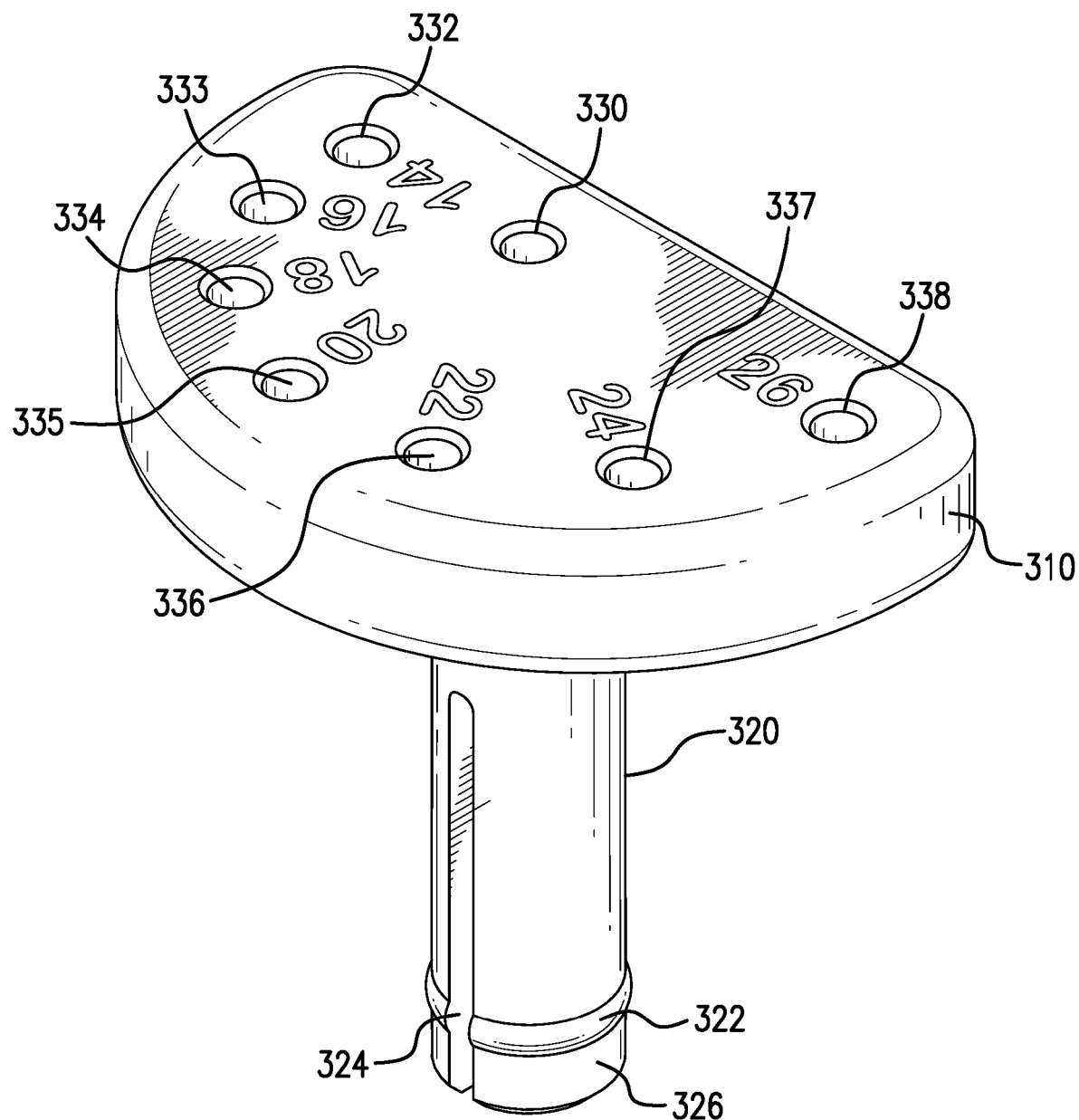
FIG. 1A is a perspective view of a parallel guide for joint fusion according to one embodiment.
Figure 1B:
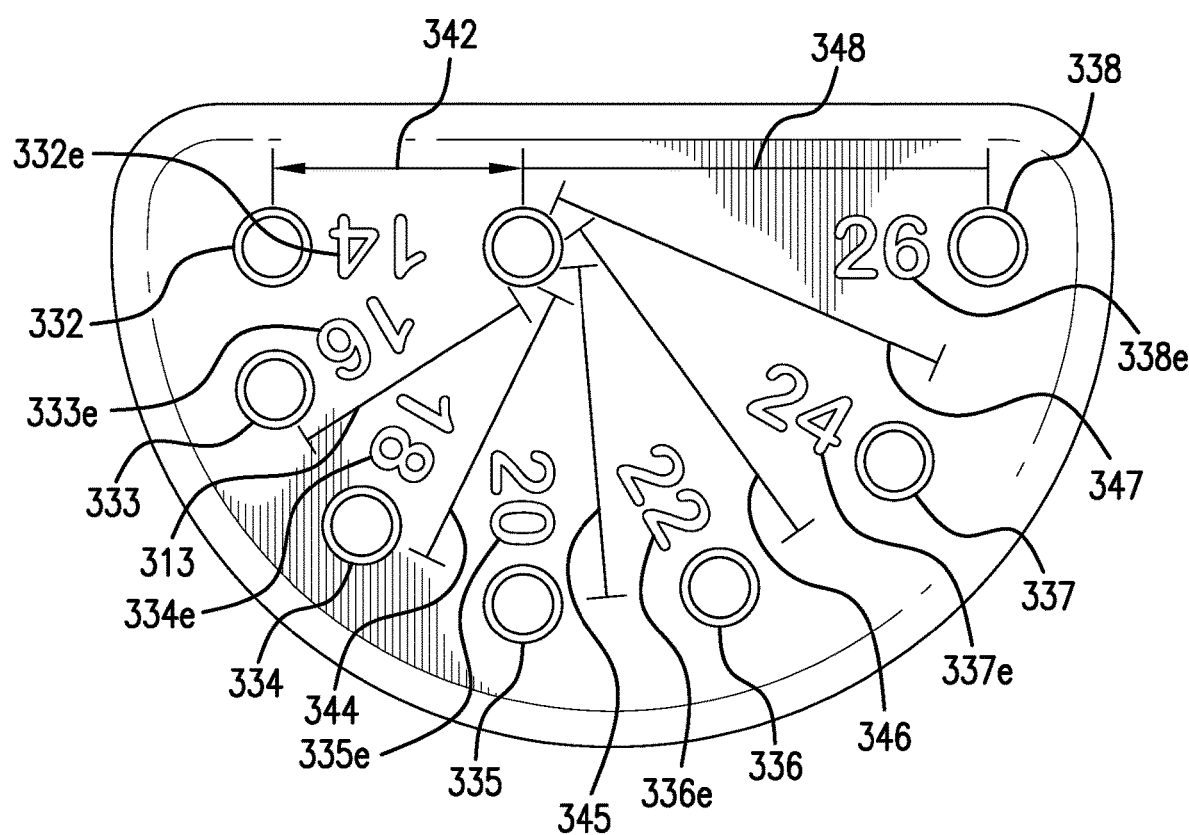
FIG. 1B is a proximal view thereof.

In the following detailed description, reference is made to the accompanying drawings, which form a part hereof. In the drawings, similar symbols typically identify similar components, unless context dictates otherwise. The illustrative examples described in the detailed description, drawings, and claims are not meant to be limiting. Other examples may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are implicitly contemplated herein.

Techniques for joint fusion are described, including systems, apparatuses and processes for fusing a joint. Systems and apparatuses for fusing a joint include a cage (i.e., a cannulated cage), a tissue protector assembly, a guide, a depth gauge, a cannulated drill bit (e.g., an adjustable cannulated drill bit that employs a stop collar), a driver, a parallel guide, and a plunger distance tool. As used herein, the term "cannulated" refers to having a cannula, or a hollow shaft. In some examples, the cage may be inserted or implanted into tissue (e.g., bone, cartilage, or other tissue in the joint). As used herein, the term "implant" or "implantation" refers to inserting or insertion into a part of a body. For example, a bone cage may be implanted into a joint (e.g., a sacroiliac joint). In some examples, the cage may have a cannula and radial fenestrations in which therapeutic materials may be packed. Such therapeutic materials may include osteogenic compounds (e.g., bone morphogenetic protein, or other osteogenic compounds that may ossify tissue in the joint), osteoconductive materials (e.g., demineralized bone, hydroxyapatite, or other material that promotes bone growth), antibiotics, steroids, contrast materials, or other materials that may beneficial to fusing the joint, treating inflammation or other conditions in the joint, or enabling the visualization of the area within and adjacent to an implanted bone cage. In some examples, the bone cage may be a screw or screw type device having threads. In some examples, the screw may have one or more rows or groups of helical fenestrations along the wall (i.e., the shaft of the cage defining the cannula) of its shaft to allow the material packed inside the cannula of the cage to contact (e.g., touch, seep into, affect, communicate with, or otherwise physically contact) tissue adjacent to, surrounding, or even within, the cage. In some examples, various tools may be used to insert a cage into a location on a joint, and to prepare the location for the insertion procedure. Such tools may include an implantation assembly, which may comprise a tissue protector; a guide; a depth gauge; a cannulated drill bit; a driver; a parallel guide; a packing plunger, which may comprise a packing tube, a plunger and a loading port; a plunger distance tool; and other tools.

In some examples, a guide may be inserted first into a joint at a desired location, in a lateral position across the joint. In some examples, a tissue protector assembly may be used, along with the guide, to guide the preparation (i.e., drilling) of a pilot hole as well as to guide insertion of a cannulated cage or other implant while forming a barrier between the preparation site and the surrounding tissue. In some examples, a cannulated drill bit may be used with the tissue protector and/or guide to drill the pilot hole. In some examples, a driver or screw driver may be used to insert the cage into the pilot hole. The terms "driver" is used herein to refer to a tool with a tip configured to engage the head of a screw or similar device, the tool being useful for rotating a screw or otherwise manipulating the screw to drive the screw or, in this case, cage into place in a joint. In some examples, a parallel spacer device may be used to space another guide in preparation for insertion of another cage. In some examples, a packing plunger assembly may be used to pack the cage with the above-mentioned materials. The packing plunger may be used to pack materials into the cage either or both pre- and post-insertion of the cage into the joint, and may be used with or without the tissue protector assembly.

FIGS. 1A-E are various views of a parallel guide 300 for joint fusion according to one embodiment. Here, the parallel guide 300 includes a parallel spacer body 310 and an external positioning protrusion 320. In accordance with various embodiments, the parallel spacer body 310 includes a plurality of apertures (e.g., apertures 330 or 332-338) suitable to receive one or more guides (e.g., guide pins 418a or 418b shown in FIGS. 3 and 8A). In accordance with various embodiments, the external positioning protrusion 320 extends from the parallel spacer body 310 and is suitable to engage with a tissue protector 400. In some examples, parallel guide 300 may be configured to place another or a next guide at a distance from a previously placed implant (i.e., a previously implanted screw or cage). Like-numbered and named elements in this view may describe the same or substantially similar elements as in previous or subsequent views.

In accordance with various embodiments, the parallel spacer body 310 includes a proximal surface 312 and a distal surface 314. While shown as opposing flat parallel surfaces, it is appreciated that these surfaces can have other suitable profiles, such as concave, convex and irregular surfaces. In accordance with various embodiments, the parallel spacer body 310 has a sufficient thickness to hold a guide in a substantially constant angular position relative to the parallel guide 300. The parallel spacer body 310 can be any suitable shape to position each of the various apertures therethrough. In one example, the proximal surface 312 is a semi-circle defining the overall shape of the parallel spacer body down to the distal surface 314 which is also a semi-circle. Other shapes, such as circles, polygons (triangles, rectangles, etc.) or less geometrical shapes may be suitable as well.

In accordance with various embodiments, the primary guide aperture (e.g., aperture 330) extends through the parallel spacer body 310. The primary guide aperture (e.g., aperture 330) includes an axis 330a that defines the orientation of the guide (e.g., guide 418) relative to the parallel guide 300 as the guide passes through the aperture. In some embodiments, the body orientation, i.e. the orientation between the parallel guide 300 (as defined by the upper surface 213) and the guide 418 is perpendicular. In other embodiments, there can be an angle less than 90 degrees between the two. The primary guide aperture (e.g., aperture 330) includes an opening 330b on the proximal end of the parallel guide 300. In one example, the opening 330b extends into the parallel spacer body 310 from the proximal surface 312. In other examples, the opening 330b may extend into the parallel spacer body 310 from any suitable surface on the proximal end of the parallel guide 300, such as a protrusion on the proximal end or like feature. The primary guide aperture (e.g., aperture 330) includes an opening 330c on the distal end of the parallel guide 300. In one example, the opening 330c extends into the parallel spacer body 310 from any suitable surface on the distal end of the parallel guide 300. For example, the aperture 330 can extend from the opening 330b to the opening 330c on distal surface 326 on the external positioning protrusion 320. In another example, the opening 330c may extend from any similar suitable feature, such as from the distal surface 314.

The primary guide aperture (e.g., aperture 330) is defined by an interior surface 330d that extends between opening 330b and 330c.

Figure 1C:
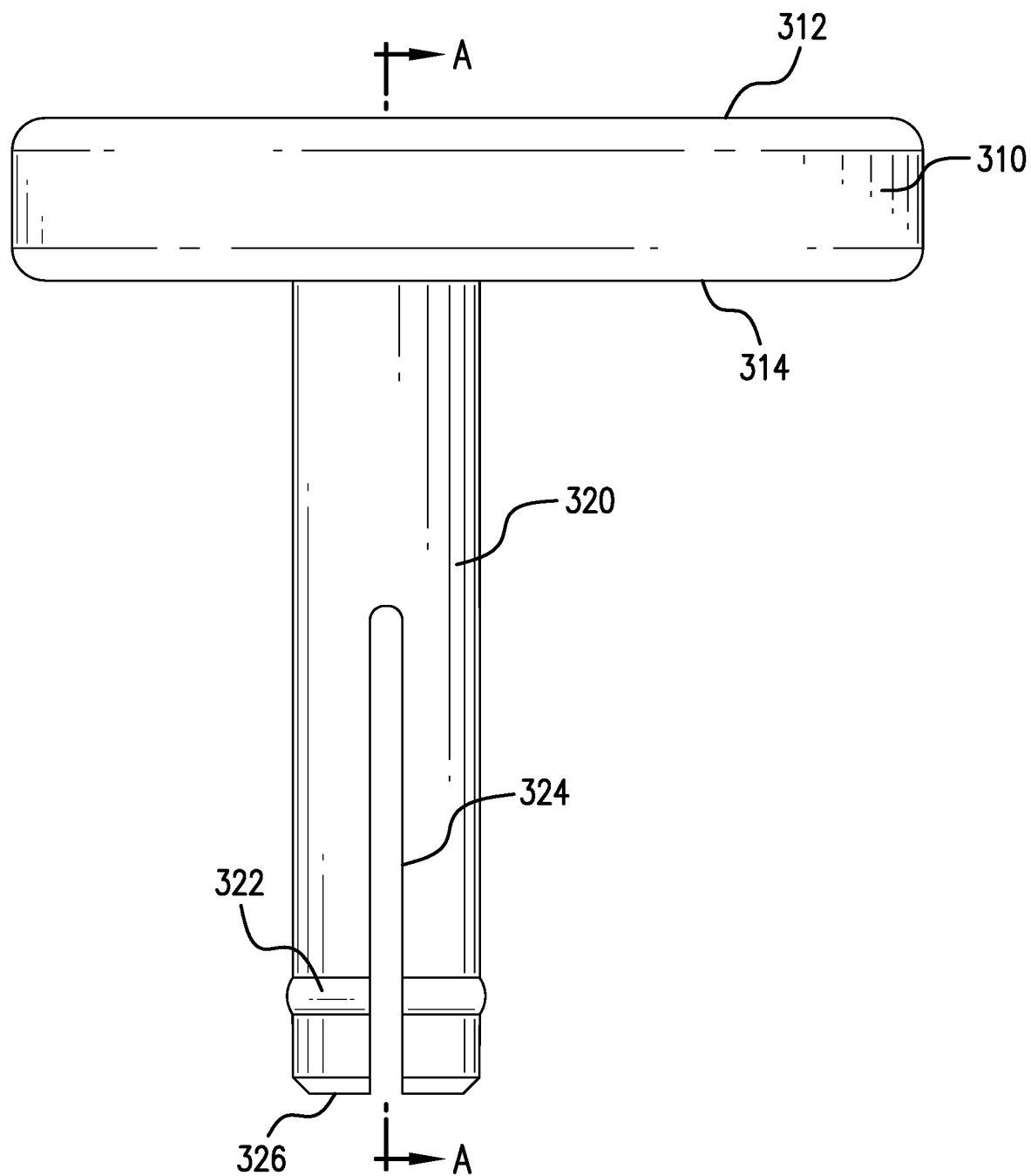
FIG. 1C is a side view thereof.
Figure 1D:
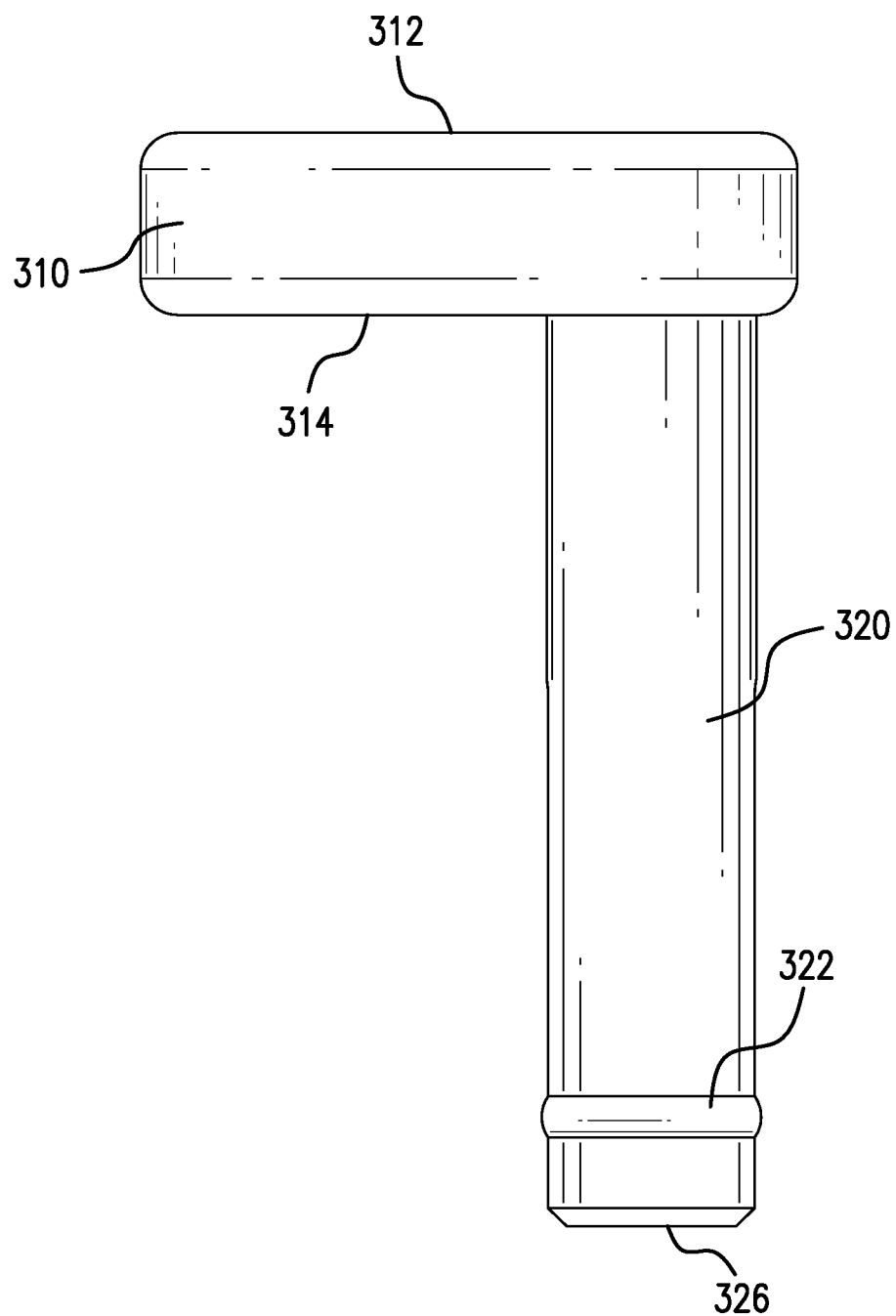
FIG. 1D is a front view thereof.
Figure 1E:
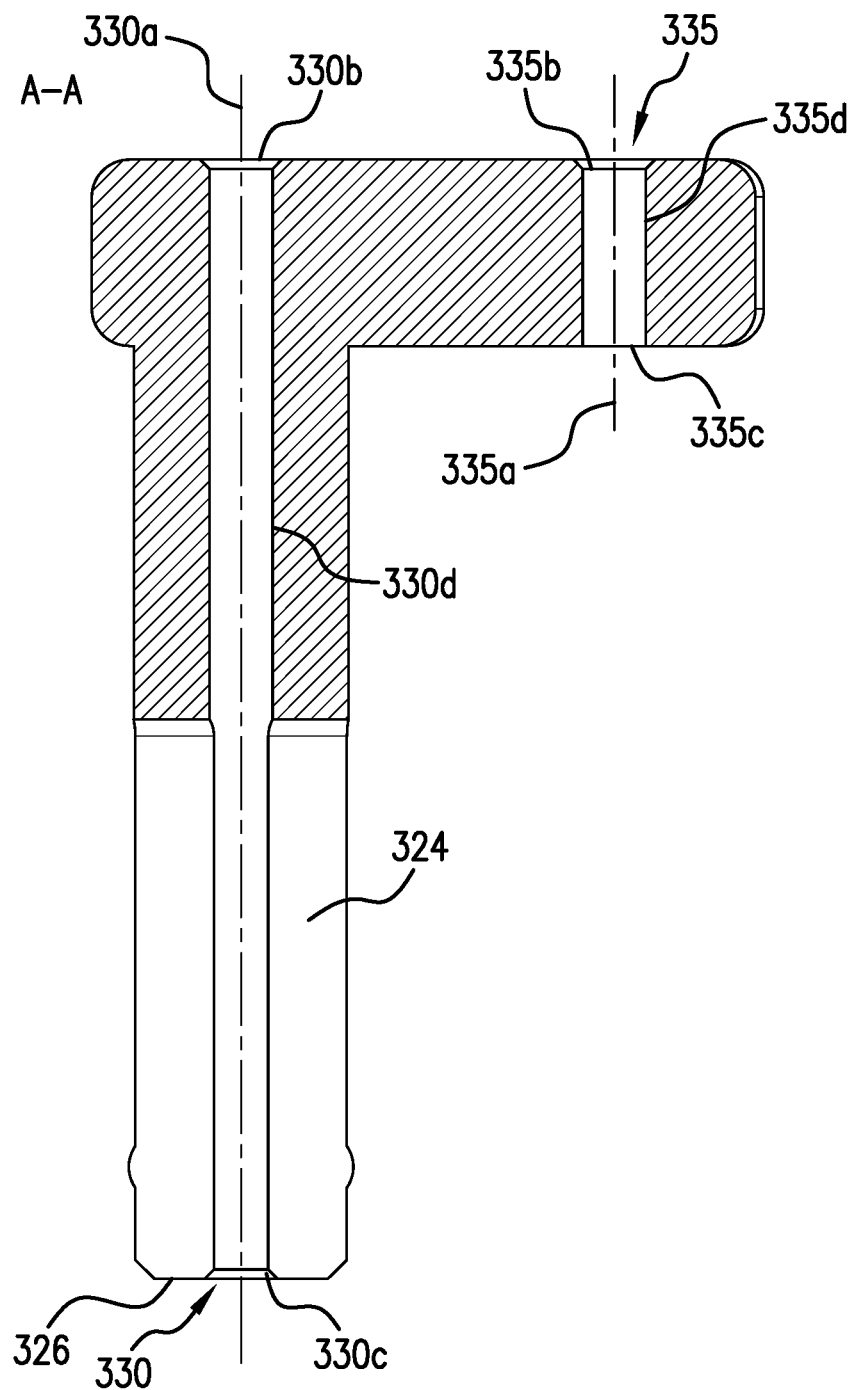
FIG. 1E is a cross-section side view taken along cross section line A-A of FIG. 1C.

In accordance with various embodiments, the parallel guide 300 includes one or more subsequent guide apertures (e.g., apertures 332-338). Each of the plurality of subsequent guide apertures (e.g., apertures 332-338) are fixedly located relative to the primary guide aperture (e.g., aperture 330) thereby defining a set distance between each of the subsequent guide apertures (e.g., apertures 332-338) and the primary guide aperture (e.g., aperture 330). The subsequent guide apertures (e.g., apertures 332-338) may be integrally formed with parallel spacer body 310 along with the primary guide aperture (e.g., aperture 330) such that each distance (e.g., distance 342-348) is constant. In accordance with various embodiments, each of the subsequent guide apertures (e.g., apertures 332-338) extends through the parallel spacer body 310. Each of the subsequent guide apertures (e.g., apertures 332-338) includes an axis (e.g., 332a-338a respectively) that defines the orientation of a new guide (e.g., guide 418b) relative to the parallel guide 300 as the guide passes through the aperture. Each of the subsequent guide apertures (e.g., apertures 332-338) includes an opening (e.g., openings 332b-338b respectively) on the proximal end of the parallel guide 300. In one example, the opening (e.g., any one of openings 332b-338b) extends into the parallel spacer body 310 from the proximal surface 312. In other examples, the opening (e.g., any one of openings 332b-338b) may extend into the parallel spacer body 310 from any suitable surface on the proximal end of the parallel guide 300, such as a protrusion on the proximal end or like feature. Each of the subsequent guide apertures (e.g., apertures 332-338) includes an opening (e.g., openings 332c-338c respectively) on the distal end of the parallel guide 300. In one example, the opening (e.g., any one of openings 332c-338c) extends into the parallel spacer body 310 from any suitable surface on the distal end of the parallel guide 300. In one example, the opening (e.g., any one of openings 332c-338c) extends from the distal surface 314 into the parallel spacer body 310. In another example, the aperture (e.g., apertures 332-338) can extend from the opening (e.g., openings 332c-338c respectively) on a distal surface on a protrusion or like feature. Each of the subsequent guide apertures (e.g., apertures 332-338) are defined by an interior surface (e.g., surface 332d-338d respectively) that extends between each respective proximal opening (e.g., openings 332c-338c respectively) and each respective distal opening (e.g., openings 332c-338c respectively). FIG. 1E illustrates an example showing aperture 335 extending from proximal opening 335b to distal opening 335c, defining the interior surface 335d.

In some examples, parallel spacer body 300 may comprise spacer markings (e.g., markings 332e-338e) with numerical labels for measuring out the spacing between the primary guide 418 and the subsequently placed guide 418b. Any subsequently placed guide 418b is placed in the aperture corresponding to the spacer marking. The number corresponding to that marking may indicate the space (i.e., distance, for example, in millimeters) between a previously placed guide 418, and the guide 418b to be placed in subsequent guide aperture (e.g., aperture 332-338). This, in turn, may determine the spacing between an implant (e.g., cage or bone screw) and a next implant (e.g., cage or bone screw). By utilizing discrete apertures, as opposed to a continuously adjustable mechanism for locating the subsequent guide relative to the primary guide, consistent control over the surgical procedure can be obtained.

In accordance with one embodiment, the pattern of discrete locations for the aperture (e.g., aperture 332-338) can form an arc. The primary aperture (e.g., aperture 330) can be concentric within the arc. In one embodiment, the concentric location is selected such that there is a different distance between the primary aperture (e.g., aperture 330) and each of the other apertures (e.g., aperture 332-338) extending through the guide body 310. This results in a variety of different discrete distances that are usable in the surgical procedure for placing one guide (e.g., pin 418b) in a parallel configuration relative to another guide (e.g., pin 418). In one example, the distances between the primary aperture (e.g., aperture 330) and each of the other apertures (e.g., aperture 332-338) increases as the arc progresses from one side to the other. The markings (e.g., markings 332e-338g) indicate this increasing distance, as shown by way of example in FIGS. 1A and 1B.

In accordance with various embodiments, the external positioning protrusion 320 is suitably connected to the parallel spacer body 310 so as to constrain and/or position the tissue protector 400 relative to the parallel spacer body 310. For example, the external positioning protrusion 320 may be integrally formed with parallel spacer body 310. In one embodiment, the external protrusion may have an outer diameter suitable to be received into the tissue protector 400. In another embodiment, the external protrusion may have an inner diameter (e.g. along the aperture 330 which could be stepped in diameters to accommodate both the guide and the tissue protector) suitable to receive the tissue protector 400. In various embodiments, the external positioning protrusion 320 may function as the primary alignment member by engaging another alignment entity such as a drill guide or tissue protector. This allows the second guide 418b to be set parallel relative to the other alignment entity.

Figure 8A:
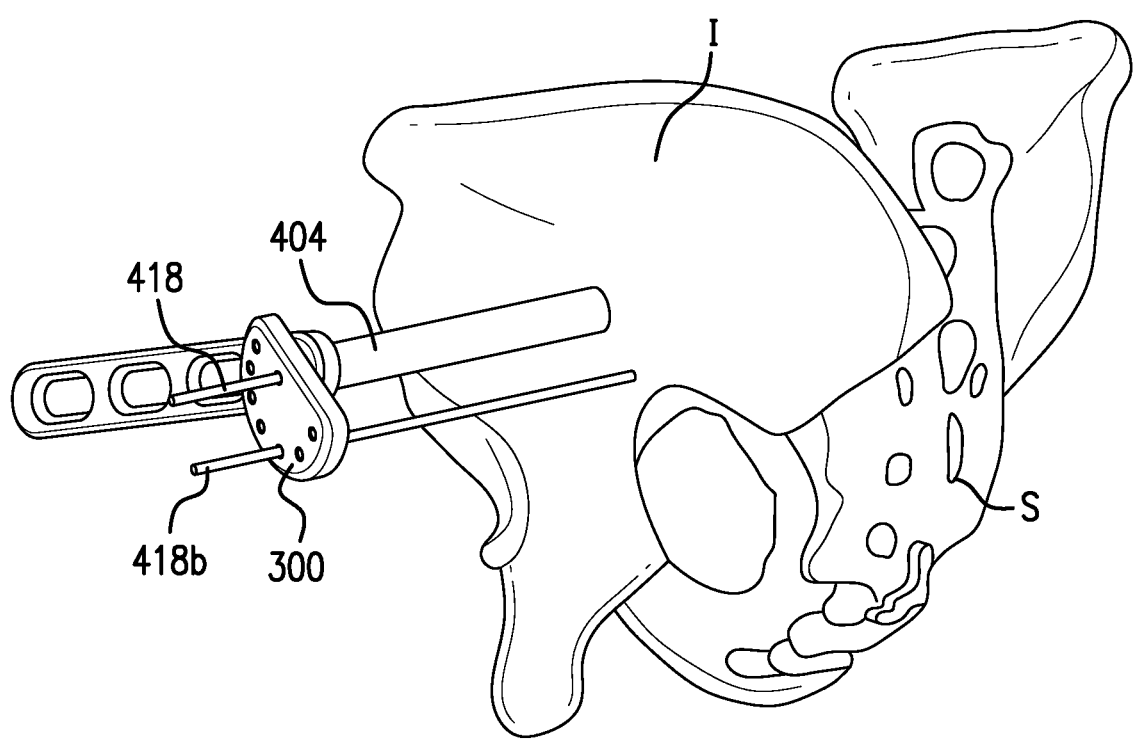
FIG. 8A is a perspective view of a parallel guide according to one embodiment being used to set a guide at a new location in a sacroiliac joint in the procedure of FIG. 3.

In some examples, external positioning protrusion 320 may be sized (i.e., have an outer diameter configured) to fit within the cannula of a drill guide, and also may have its own hollow shaft (i.e., an external positioning protrusion cannula) configured to fit around or over a guide. FIG. 8A illustrates a view of an exemplary parallel guide 300 for placement of another guide as placed on a drill guide: the parallel spacer body 310, external positioning protrusion 320, primary guide aperture 330, subsequent guide aperture 332, tissue protector 404, handle 412, and guide 418b. As shown, external positioning protrusion 320 may fit into tissue protector 404. In some embodiments, part of parallel spacer body may rest against tissue protector. In various embodiments, guide 418 may be inserted into the joint (e.g., by threading, hammer, pressing or similar method). A depth gauge may be used to measure the depth of the guide 418 into the joint. In some embodiments, the tissue protector 404 may be slid over the depth gauge 602 to locate the tissue protector 404, or in other embodiments, the tissue protector 404 may be located first and then the guide (e.g. pin 418) and depth gauge 602 are inserted into the tissue protector 404. The external positioning protrusion 320 may fit over guide 418 via aperture 330. In some examples, parallel guide 300 is placed on tissue protector 404. In some embodiments, external positioning protrusion 320 may be inserted into the tissue protector. The external positioning protrusion 320 may flex by closing the slot 324 as it is forced into the tissue protector with the annular ridge 322 engaging the internal wall of the tissue protector 404. A next guide 418b, as shown in FIG. 8A, may be inserted through any one of the subsequent guide apertures (e.g., any one of apertures 332-338) until the end of the next guide 418b rests against a bone (i.e., an ilium). While in place in subsequent guide aperture (e.g., any one of apertures 332-338), the next guide 418b may be advanced into the bone and through a joint to a desired depth (e.g., using a mallet or other suitable method).

In some examples, parallel spacer body 300 may comprise spacer markings (e.g., markings 332e-338g) with numerical labels for measuring out the spacing between the primary guide 418 and the subsequently placed guide 418b. Any subsequently placed guide 418b is placed in the aperture corresponding to the spacer marking. The number corresponding to that marking may indicate the space (i.e., distance, for example, in millimeters) between a previously placed guide 418, and the guide 418b to be placed in subsequent guide aperture (e.g., aperture 332-338). This, in turn, may determine the spacing between an implant (e.g., cage or bone screw) and a next implant (e.g., cage or bone screw).

FIGS. 2A-F are various views of a parallel guide for joint fusion according to one embodiment. Here, the parallel guide 350 includes a parallel spacer body 360 and an external positioning protrusion 370. In accordance with various embodiments, the parallel spacer body 310 includes a plurality of apertures (e.g., apertures 380 or 382-337) suitable to receive one or more guides (e.g., guides 418a or 418b shown in FIGS. 3 and 8B). In accordance with various embodiments, the external positioning protrusion 370 extends from the parallel spacer body 360 and is suitable to engage with a tissue protector 400. In some examples, parallel guide 350 may be configured to place another or a next guide at a distance from a previously placed implant (i.e., a previously implanted screw or cage). Like-numbered and named elements in this view may describe the same or substantially similar elements as in previous or subsequent views.

In accordance with various embodiments, the parallel spacer body 360 includes a proximal surface 362 and a distal surface 364. While shown as opposing flat parallel surfaces, it is appreciated that these surfaces can have other suitable profiles, such as concave, convex and irregular surfaces. In accordance with various embodiments, the parallel spacer body 360 has a sufficient thickness to hold a guide in a substantially constant angular position relative to the parallel guide 350. The parallel spacer body 360 can be any suitable shape to position each of the various apertures therethrough. In one example, the proximal surface 362 is an elongated rectangle defining the overall shape of the parallel spacer body down to the distal surface 364 which is also a semi-circle. Other shapes, such as circles, polygons (triangles, other rectangles, etc.), or less geometrical shapes may be suitable as well.

In accordance with various embodiments, the primary guide aperture (e.g., aperture 380) extends through the parallel spacer body 360. The primary guide aperture (e.g., aperture 380) includes an axis 380a that defines the orientation of the guide (e.g., guide 418) relative to the parallel guide 350 as the guide passes through the aperture. The primary guide aperture (e.g., aperture 380) includes an opening 380b on the proximal end of the parallel guide 350. In one example, the opening 380b extends into the parallel spacer body 360 from the proximal surface 362. In other examples, the opening 380b may extend into the parallel spacer body 360 from any suitable surface on the proximal end of the parallel guide 350, such as a protrusion on the proximal end or like feature. The primary guide aperture (e.g., aperture 380) includes an opening 380c on the distal end of the parallel guide 350. In one example, the opening 380c extends into the parallel spacer body 360 from any suitable surface on the distal end of the parallel guide 350.

For example, the aperture 380 can extend from the opening 380b to the opening 380c on distal surface 376 on the external positioning protrusion 370. In another example, the opening 380c may extend from any similar suitable feature, such as from the distal surface 364. The primary guide aperture (e.g., aperture 380) is defined by an interior surface 380d that extends between opening 380b and 380c.

In accordance with various embodiments, the parallel guide 350 includes one or more subsequent guide apertures (e.g., apertures 382-387). Each of the plurality of subsequent guide apertures (e.g., apertures 382-387) are fixedly located relative to the primary guide aperture (e.g., aperture 380) thereby defining a set distance between each of the subsequent guide apertures (e.g., apertures 382-387) and the primary guide aperture (e.g., aperture 380). The subsequent guide apertures (e.g., apertures 382-387) may be integrally formed with parallel spacer body 360 along with the primary guide aperture (e.g., aperture 380) such that each distance (e.g., distance 392-398) is constant. In accordance with various embodiments, each of the subsequent guide apertures (e.g., apertures 382-387) extends through the parallel spacer body 310. Each of the subsequent guide apertures (e.g., apertures 382-387) includes an axis (e.g., 382a-387a respectively) that defines the orientation of a new guide (e.g., guide 418b) relative to the parallel guide 350 as the guide is located through the aperture. Each of the subsequent guide apertures (e.g., apertures 382-387) includes an opening (e.g., openings 382b-387b respectively) on the proximal end of the parallel guide 300. In one example, the opening (e.g., any one of openings 382b-387b) extends into the parallel spacer body 360 from the proximal surface 362. In other examples, the opening (e.g., any one of openings 382b-387b) may extend into the parallel spacer body 360 from any suitable surface on the proximal end of the parallel guide 350, such as a protrusion on the proximal end or like feature. Each of the subsequent guide apertures (e.g., apertures 382-387) includes an opening (e.g., openings 382c-387c respectively) on the distal end of the parallel guide 350. In one example, the opening (e.g., any one of openings 382c-387c) extends into the parallel spacer body 360 from any suitable surface on the distal end of the parallel guide 350. In one example, the opening (e.g., any one of openings 382c-387c) extends from the distal surface 364 into the parallel spacer body 360. In another example, the aperture (e.g., apertures 382-387) can extend from the opening (e.g., openings 382c-387c respectively) on a distal surface on a protrusion or like feature. Each of the subsequent guide apertures (e.g., apertures 382-387) is defined by an interior surface (e.g., surface 338d-387d respectively) that extends between each respective proximal opening (e.g., openings 382c-387c respectively) and each respective distal opening (e.g., openings 382c-387c respectively).

Figure 2A:
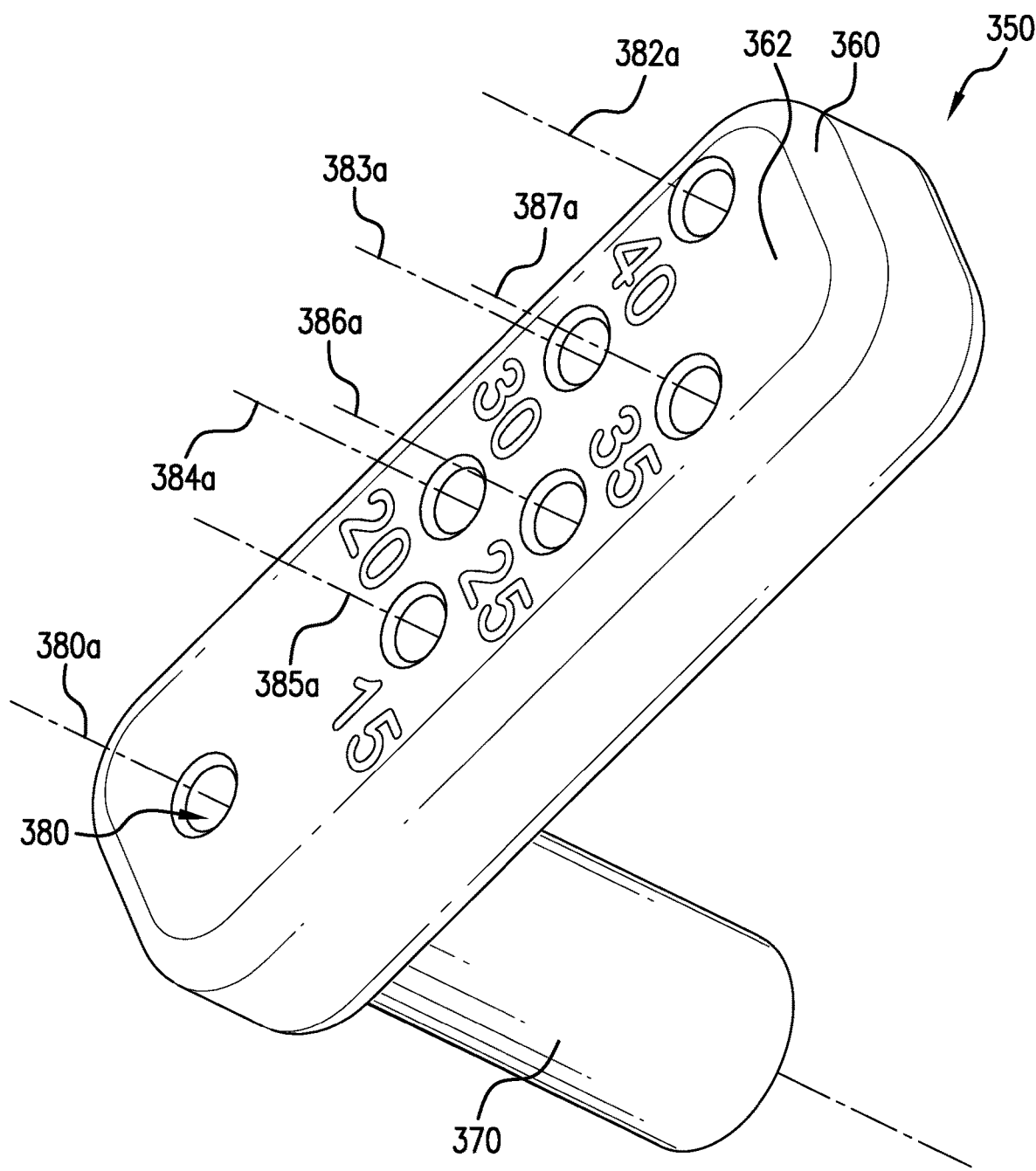
FIG. 2A is a perspective view of a parallel guide for joint fusion according to one embodiment.
Figure 2B:
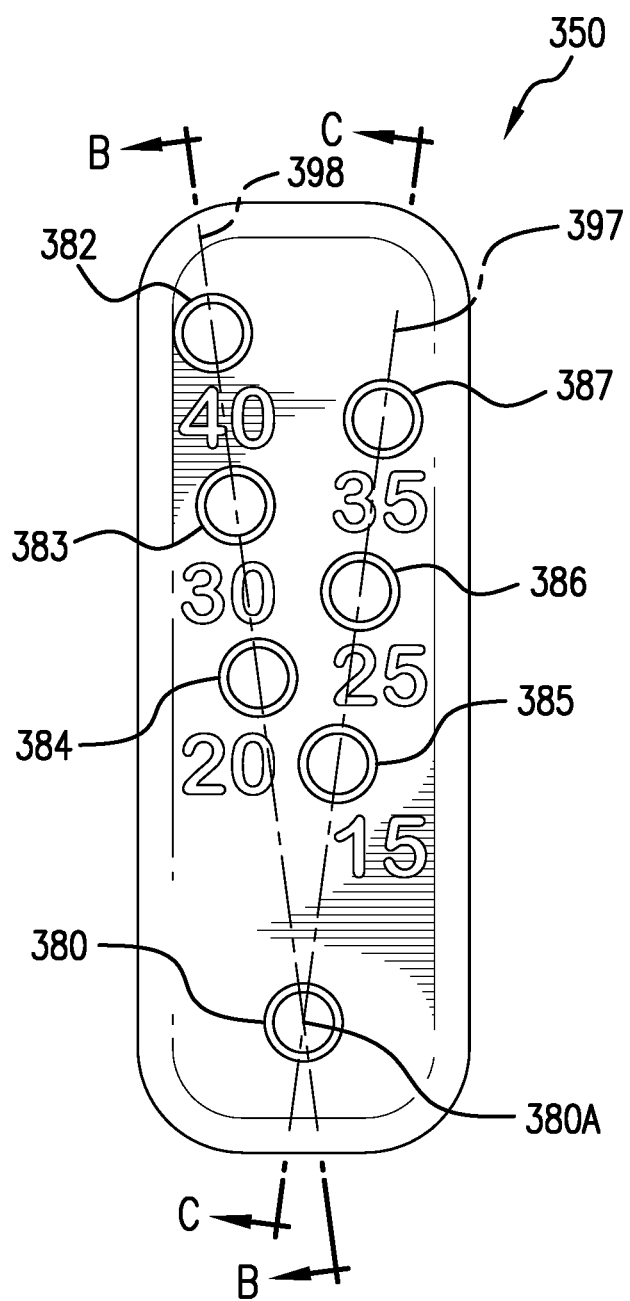
FIG. 2B is a proximal end view thereof.
Figure 2C:
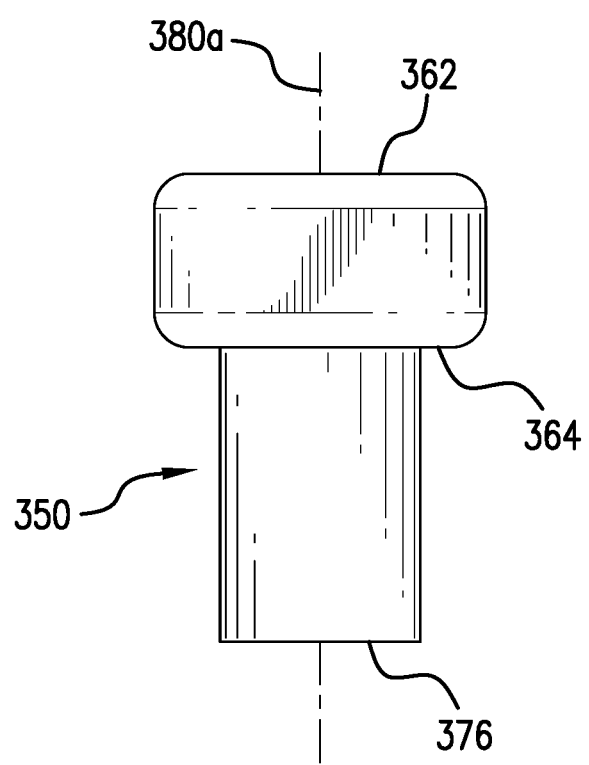
FIG. 2C is a side view thereof.
Figure 2D:
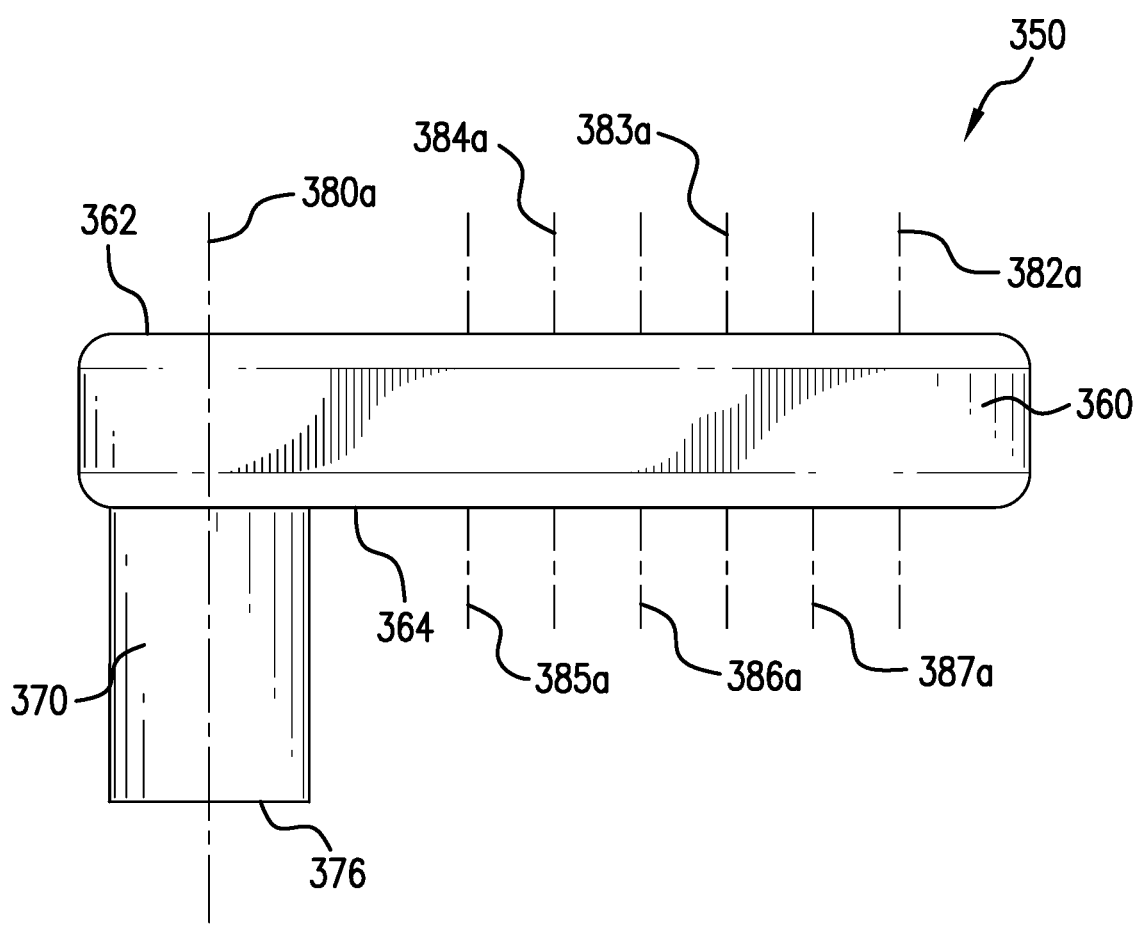
FIG. 2D is a side view thereof.
Figure 2E:
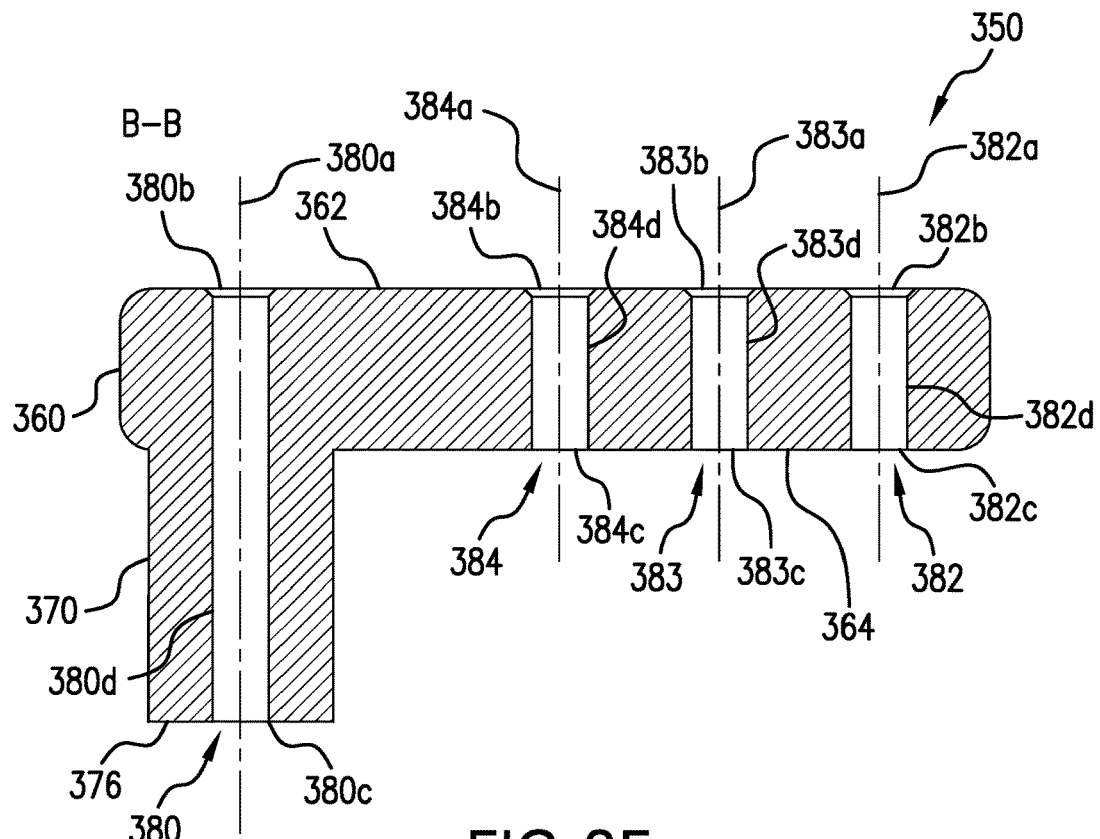
FIG. 2E is a cross-section view taken along line B-B of FIG. 2B.
Figure 2F:
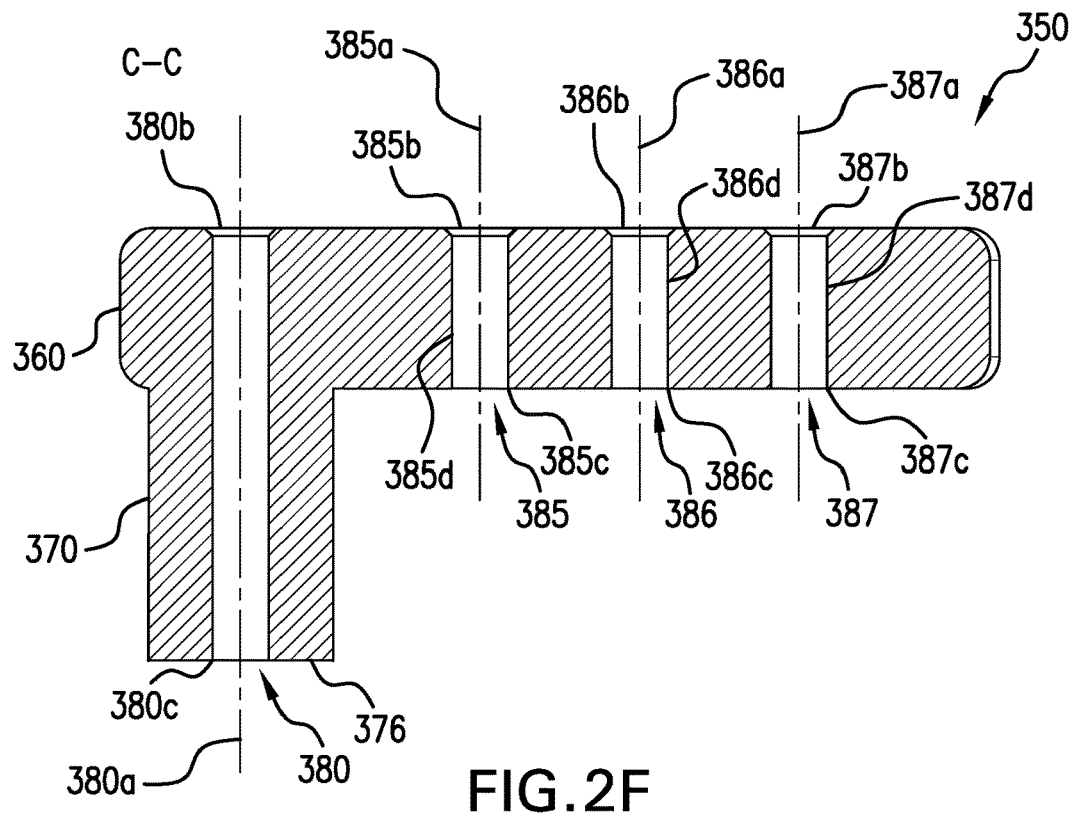
FIG. 2F is a cross-section view taken along line C-C of FIG. 2B

FIG. 2E is a cross-section view taken along line B-B of FIG. 2B. FIG. 2E illustrates an example showing apertures 385, 386, and 387 extending from proximal openings 385b, 386b and 387b respectively to distal openings 385c, 386c and 387c respectively, defining the interior surface 385d, 386d, and 387d respectively. FIG. 2F is a cross-section view taken along line C-C of FIG. 2B. FIG. 2F illustrates an example showing apertures 384, 383, and 382 extending from proximal openings 384b, 383b and 382b respectively to distal openings 384c, 383c and 382c respectively, defining the interior surface 384d, 3863, and 382d respectively.

In some examples, parallel spacer body 350 may comprise spacer markings (e.g., markings 382e-387g) with numerical labels for measuring out the spacing between the primary guide 418 and the subsequently placed guide 418b.

Any subsequently placed guide 418*b* is placed in the aperture corresponding to the spacer marking. The number corresponding to that marking may indicate the space (i.e., distance, for example, in millimeters) between a previously placed guide 418, and the guide 418*b* to be placed in subsequent guide aperture (e.g., aperture 382-387). This, in turn, may determine the spacing between an implant (e.g., cage or bone screw) and a next implant (e.g., cage or bone screw). By utilizing discrete apertures, as opposed to a continuously adjustable mechanism for locating the subsequent guide relative to the primary guide, consistent control over the surgical procedure can be obtained.

In accordance with one embodiment, the pattern of discrete locations for the aperture (e.g., aperture 382-387) can extend from aperture 380 in separate linear formation. As indicated above, each of the apertures (e.g., apertures 382-387) can form a separate line with aperture 380 being the first point and apertures 382-387 being separate distinct separate points forming separate lines with aperture 380. However, as illustrated in FIGS. 2A-2F, to form a smaller body, 360 each of the apertures (e.g., aperture 382-387) can group together into separate lines. For example half of the apertures can be in one line and half of the apertures can be in the other. The apertures can alternate between lines with increasing distance from aperture 380. For example, apertures (e.g., apertures 382-387) can increase in distances from aperture 380 in according to a progression: aperture 385, then aperture 384, then aperture 386, then aperture 383, then aperture 387, then aperture 382. But each of apertures 385, 386, and 387 can fall along one line 397 from aperture 380 and each of apertures 384, 383, and 382 can fall along another line 398 from aperture 380. This arrangement allows smaller steps in distances between apertures, without the aperture contacting each other. In one example, each of the apertures in a line (e.g. line 398) are separated from each by about the distance of one aperture diameter. This results in that ability to step the apertures alternatively between the lines in steps equal to the aperture diameter. In another example, each of the apertures in a line can be separated from one another by a distance of less than the aperture diameter. This results in that ability to step the apertures alternatively between the lines in steps less than the aperture diameter. In another example, each of the apertures in a line can be separated from one another by a distance of more than the aperture diameter. Additionally, more lines of apertures can be incorporated. In effect, a combination of guide 300 and 350 can be combined with multiple lines forming multiple arcs giving significant precision to pin location while still providing discrete apertures for better consistency. The primary aperture (e.g., aperture 380) can be more concentric within the arc. The markings (e.g., markings 382*e*-387*g*) indicate this increasing distance, as shown by way of example in FIGS. 2A and 2B.

In accordance with various embodiments, the external positioning protrusion 370 is suitably connected to the parallel spacer body 360 so as to constrain and/or position the tissue protector 400 relative to the parallel spacer body 360. For example, the external positioning protrusion 370 may be integrally formed with parallel spacer body 360.

In some examples, external positioning protrusion 370 may be sized (i.e., have an outer diameter configured) to fit within the cannula of a drill guide and also may have its own hollow shaft (i.e., an external positioning protrusion cannula) configured to fit around or over a guide. FIG. 8A illustrates a view of an exemplary parallel guide 350 for placement of another guide as placed on a drill guide: the parallel spacer body 360, external positioning protrusion 370, primary guide aperture 380, subsequent guide aperture (e.g., aperture 382-387), tissue protector 404, handle 412 and guide 418*b*. As shown, external positioning protrusion 370 may fit into tissue protector 404. In some embodiments, part of parallel spacer body may rest against tissue protector. In various embodiments, guide 418 may be inserted into the joint (e.g., by threading, hammer, pressing or similar method). A depth gauge may be used to measure the depth of the guide 418 into the joint. In some embodiments, the tissue protector 404 may be slid over the depth gauge 602 to locate the tissue protector 404, or in other embodiments, the tissue protector 404 may be located first and then the guide (e.g. pin 418) and depth gauge 602 are inserted into the tissue protector 404. The external positioning protrusion 370 may fit over guide 418 via aperture 380. In some examples, parallel guide 350 is placed on tissue protector 404. In some embodiments, external positioning protrusion 370 may be inserted into the tissue protector. The external positioning protrusion 370 may flex by closing the slot as it is forced into the tissue protector with the annular ridge engaging the internal wall of the tissue protector 404. A next guide 418*b*, as shown in FIG. 8A, may be inserted through any one of the subsequent guide apertures (e.g., any one of apertures 382-387) until the end of the next guide 418*b* rests against a bone (i.e., an ilium). While in place in subsequent guide aperture (e.g., any one of apertures 382-387), the next guide 418*b* may be advanced into the bone and through a joint to a desired depth (e.g., using a mallet or other suitable method).

In some examples, parallel spacer body 350 may comprise spacer markings (e.g., markings 382*e*-387*g*) with numerical labels for measuring out the spacing between the primary guide 418 and the subsequently placed guide 418*b*. Any subsequently placed guide 418*b* is placed in the aperture corresponding to the spacer marking. The number corresponding to that marking may indicate the space (i.e., distance, for example, in millimeters) between a previously placed guide 418, and the guide 418*b* to be placed in subsequent guide aperture (e.g., aperture 382-387) This, in turn, may determine the spacing between an implant (e.g., cage or bone screw) and a next implant (e.g., cage or bone screw).

Figure 3:
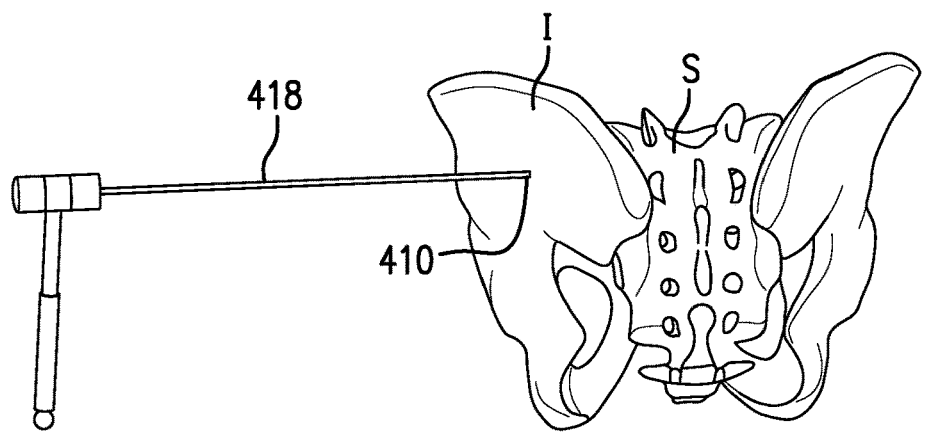
FIG. 3 illustrates a guide pin being set in a sacroiliac joint according to one embodiment of a surgical procedure for joint fusion.

FIG. 3 illustrates an exemplary guide 418. In some examples, guide 418 may be a medical grade sterile metal guide such as a wire or pin (e.g., Kirschner wire, Steinmann pin, or other metal pin) suitable for use in medical procedures. In some examples, the guide may be another type of medical device suitable to forma primary orientation during surgery. Such alternative guides can include drill guides or tissue protectors. In some examples, guide 418 may be used for alignment and guidance of a tissue protector (e.g., tissue protector 404), an implant (e.g., a cage or other implant), and other tools into the ilium I, the sacrum S, or the joint there between. The guide 418 can be set into the patient via twisting, hammering, pressure or any other suitable method. In a particular example, mallet 417 drives the guide 418 into the ilium and/or the sacrum. In some examples, guide tip 410 may form a trocar for introducing tissue protector assembly 400 into a bone.

Figure 4A:
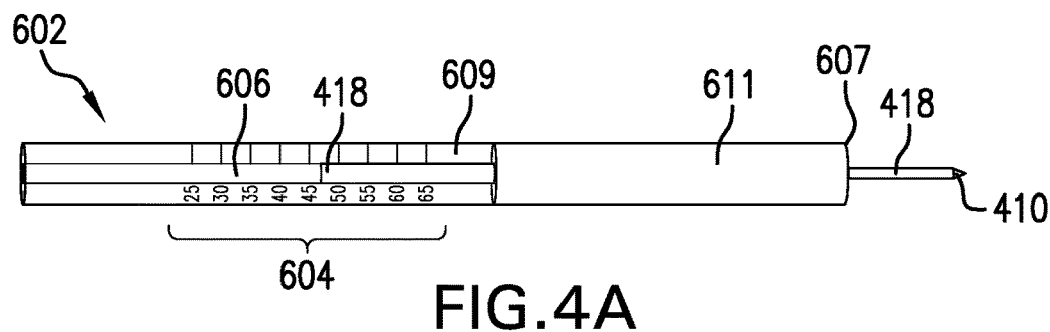
FIG. 4A illustrates a depth gauge according to one embodiment for determining the depth of a pilot hole to be drilled for insertion of a cage for joint fusion.
Figure 4B:
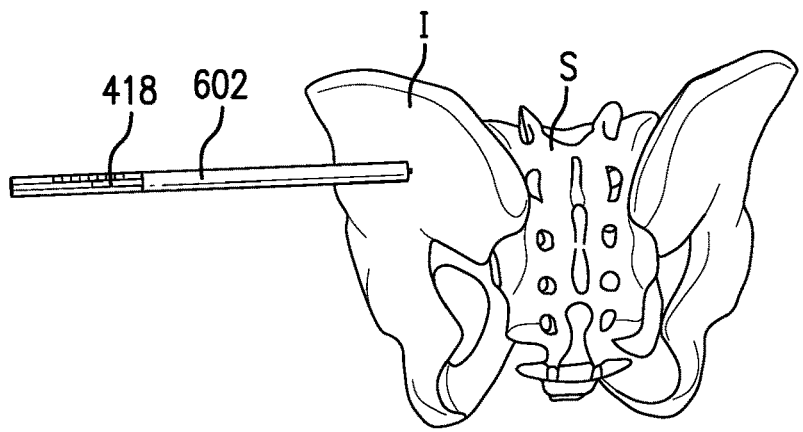
FIG. 4B is a view thereof installed over a guide being set in a sacroiliac joint in the procedure of FIG. 3.

FIG. 4A illustrates an embodiment of a depth gauge 602 for determining the depth of a guide to be inserted into the ilium I and/or sacrum S. In various embodiments, depth gauge 602 includes depth markings 604, channel 606, and distal contact surface 607. In various examples, the channel 606 is formed along an exposed wall 609 of the depth gage. The channel 606 transitions into an enclosed channel through a lower body portion 611. The contact surface 607 is located on the distal end of the lower body portion 611 and is suitable to contact the ilium I. The guide 418 may then be slid into the depth gauge 602 to the desired depth as measured on the depth markings 604. In some examples, depth gauge 602 may be configured to determine the depth in which guide 418 is inserted into a bone and/or joint. In some examples, depth gauge 602 may include depth markings 604, which can measure the depth in which the guide 418 is driven into the ilium. In some examples, depth markings 604 may indicate a range of 25-65 mm depths. In other examples, depth gauge 602 may have different depth markings, and thus indicate a different range of depths. The number in depth markings 604 that corresponds to the location of the end of guide 418 may indicate the depth of guide 418. In other examples, depth markings 604 can indicate a different depth that may correspond and be calibrated to the depth of guide 418 (e.g., depth markings 604 may indicate a desired drilling depth for a pilot hole, a depth of a cage to be implanted, or other depth that is associated with the depth of guide 418, and may thus be measured against the depth of guide 418). In still other examples, depth gauge 602 may include more or fewer elements and is not limited to the examples described.

Figure 5A:
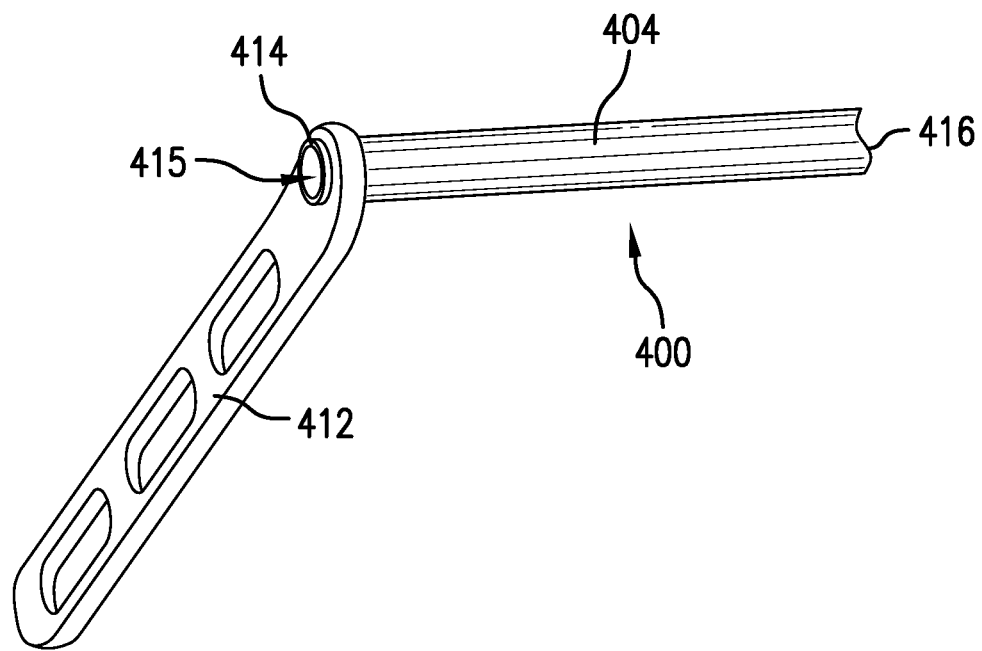
FIG. 5A illustrates a tissue protector according to one embodiment.
Figure 5B:
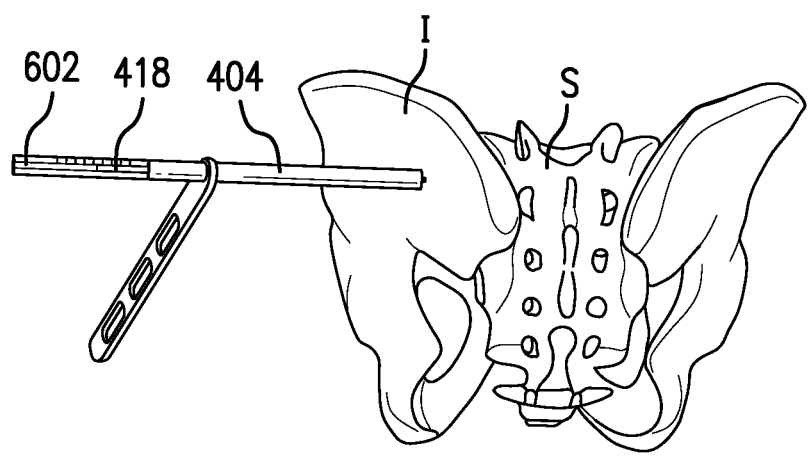
FIG. 5B is a view thereof placed over a guide and set in a sacroiliac joint in the procedure of FIG. 3.

FIGS. 5A and 5B illustrate a tissue protector assembly 400. The tissue protector assembly may include sleeve 404 and handle 412. In some examples, tissue protector sleeve 404 may include a tissue protector head 414, and tissue protector tip 416. In some examples, sleeve 404 has a hollow shaft 415 having a close fit to one or more of the depth gauge 602, the cage 100, and or a drill 700. In some embodiments, the guide 481 may be utilized with a guide sleeve. The guide sleeve can receive into the guide sleeve. The guide sleeve can then be inserted into the tissue protector. In various embodiments, the guide sleeve includes a close tolerance to the interior of the channel 415 of the tissue protector so that the guide is accurately positioned in the tissue protector 404. In some embodiments, the guide 418 is centered in the tissue protector 400. In other embodiments, the depth gauge 602 functions as the guide sleeve. In some examples, the outer diameter of sleeve (e.g., depth gauge 602) shaft is shaped to fit inside the cannula of tissue protector 400, which has an internal diameter that may be configured to accommodate tools and implants (e.g., cages 100, and the like) having a larger diameter than a guide. For example, the diameter of tissue protector 404's cannula 415 may correspond to (i.e., be sized to fit) the head or outer diameter on an implant (e.g., cages 100). In some examples, the internal surface of tissue protector 400 may be configured to guide an implant (e.g., cage 100) inserted into tissue protector 400 from tissue protector head 414 and through to tissue protector tip 416.

In some examples, tissue protector tip 416 may have spikes, teeth, wedges, or other structures, to engage a bone. As shown, tissue protector tip 416 is engaged with an ilium (i.e., its spikes, teeth, wedges or other structure for engaging a bone, are embedded in the ilium). In some embodiments, the tissue protector tip 416 does not embed into the bone but merely increases friction such that the tissue protector tip 416 does not slip on the exterior of the bone. In other examples, tissue protector assembly 400 may be formed differently and is not limited to the examples described.

FIG. 5B illustrates an exemplary tissue protector assembly placed over a guide. Here, diagram 420 may include tissue protector sleeve 404, handle 412, tissue protector head 414, tissue protector tip 416 and guide 418 and depth gage 602 (functioning as a guide sleeve for a pin or wire). Like-numbered and named elements in this view may describe the same or substantially similar elements as in previous views (e.g., FIG. 4A).

Figure 6A:
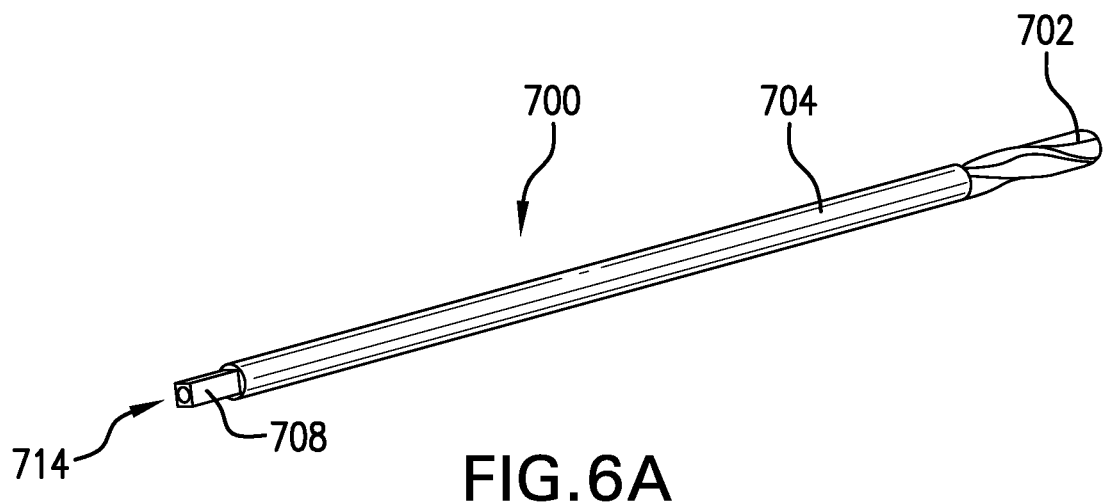
FIG. 6A is a perspective view of a cannulated drill bit for drilling a pilot hole for insertion of a cage for joint fusion according to one embodiment and FIG. 6B is a side view thereof being placed over the guide for drilling a pilot hole for insertion of a cage for joint fusion in the procedure of FIG. 3.
Figure 6B:
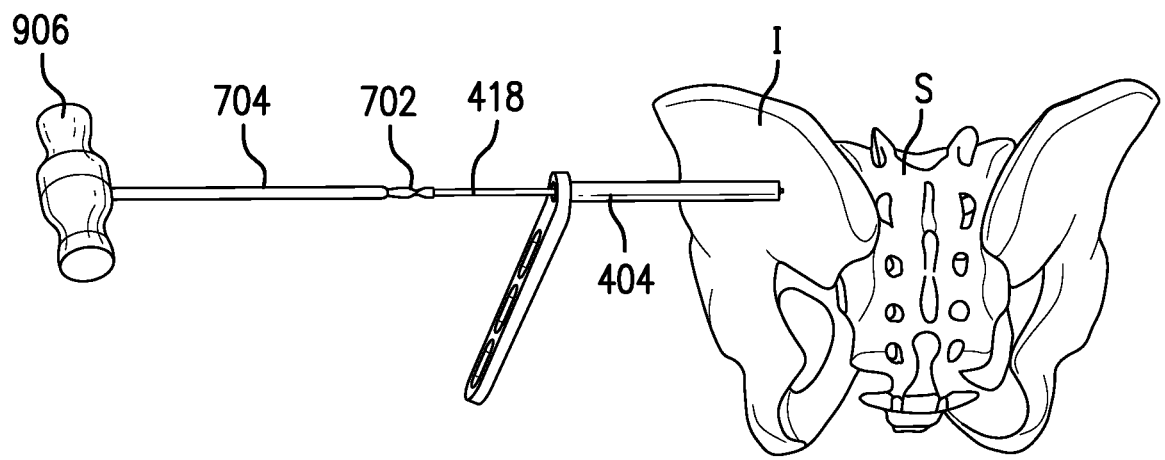

FIGS. 6A and 6B illustrates a side view of an exemplary cannulated drill bit and for drilling a pilot hole for insertion of a cage for joint fusion. Here, cannulated drill bit 700 may include cutting tip 702, body 704, and shank 709. As used herein, "drill bit" refers to any cutting tool configured to create substantially cylindrical holes, and "shank" refers to an end of the drill bit, usually the end opposite the cutting tip, configured to be grasped by a chuck of a drill, handle or other torque applying device. In some examples, cannulated drill bit 700 may be configured to drill a pilot hole to a predetermined depth. For example, cutting tip 702 may be configured to cut cylindrical holes into a bone and/or joint when torque and axial force is applied to rotate cutting tip 702 (i.e., by a drill). In some examples, cannulated drill bit 700 may be adjustable, and thereby configured to drill a range of depths using depth markings. The outside diameter of cannulated drill bit 700 may be configured to fit within a tissue protector (e.g., tissue protector 400). In some examples, the outside diameter may be significantly smaller than the tissue protector 400, such that the tissue protector does not provide significant support to the drill bit 700 or function as the primary locating tool for the drill bit 700. In other examples, the tissue protector 400 may function as the drill guide, providing significant support and locating functionality to the drill bit 700 by having an inner diameter that is substantially the same size as the outer diameter of the drill bit 700. The variance in sizes being sufficient to allow the drill bit 700 to slide and rotate within the tissue protector.

In some examples, a desired drilling depth (i.e., depth of a pilot hole) may be the same or similar to the depth of a guide that has been inserted into a bone and/or joint. In other examples, the desired drilling depth may be offset (i.e., less deep) by a predetermined amount (e.g., a few millimeters or other offset amount). For example, if a guide has been inserted 40 mm deep into the sacroiliac joint, a corresponding desired drilling depth for the pilot hole may be 40 mm, or it may be 40 mm minus the predetermined offset may be selected (i.e., if the predetermined offset is 3 mm, then the desired drilling depth in this example would be 37 mm).

The cannulated drill bit 700 includes cannula 714. In some examples, cannula 714 are sized to fit over a guide (e.g., guide 418). A driver handle 906 may receive the shank 709 allowing a user to apply a torque to the drill bit 700. The drill bit 700 may be slid down over the guide wire 418 thereby accurately locating the drill bit 700 based on the insertion location of the guide wire 418 into the bone. Tissue protector 400, particularly the sleeve 404 thereof protects the tissue surrounding the drill site from being damaged by the drilling action. The drill may than form hole through one or more bones (e.g., ilium I and/or Sacrum S).

Figure 7A:
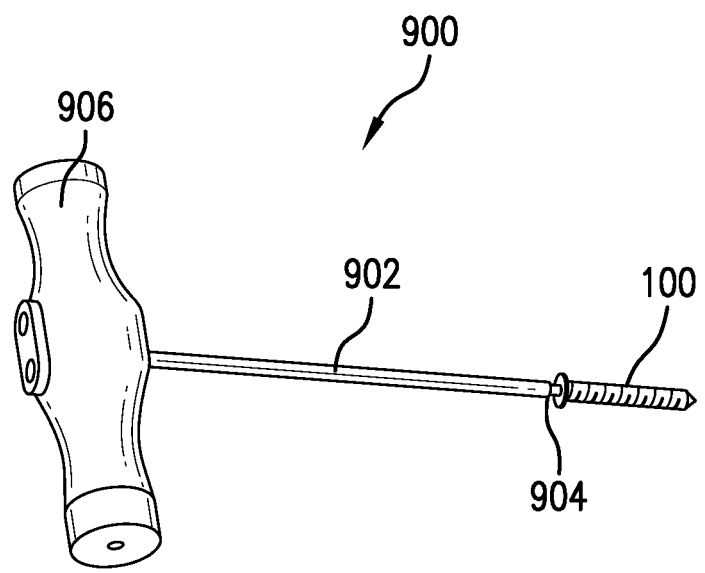
FIG. 7A is a perspective view of a driver for driving a bone cage for insertion of the cage for joint fusion according to one embodiment.
Figure 7C:
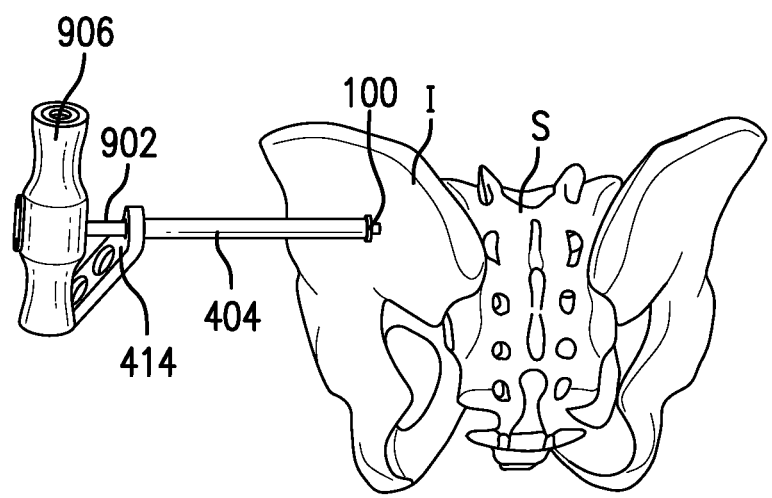
FIG. 7C is a side view of the driver of FIG. 7A driving a bone cage into a joint for fusion in the procedure of FIG. 3.
Figure 7B:
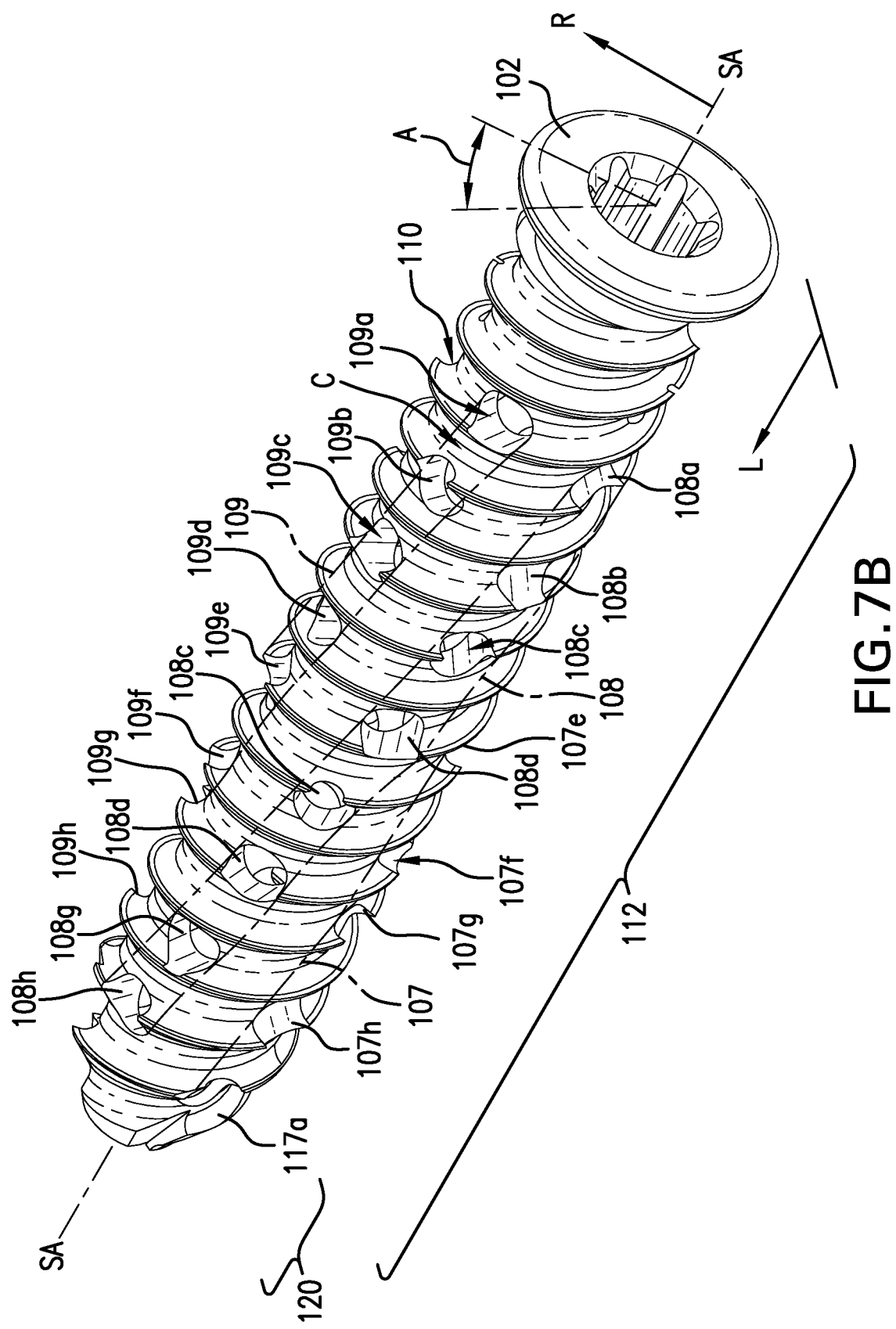
FIG. 7B is a perspective view of a bone cage shown in FIG. 7A.

FIGS. 7A and 7C illustrate an exemplary driver 902 for inserting an implant into the joint for fusion. As used herein a cage 100 is provided as an example but it is noted that bone screws for joint fusion can also be used in accordance with the various embodiments discussed herein. The bone cage 100 is further disclosed in co-pending application entitled "Bone Cage With Helically Arranged Fenestrations" having application Ser. No. 15/798,984 filed herewith on the same date, which is incorporated herein by reference in its entirety. For reference purposes, FIG. 7B illustrate a perspective view of an exemplary bone cage 100. In accordance with various embodiments, the cage 100 includes head 102, tip 104, one or more groups of helical fenestrations (e.g., fenestration groups 107-110), threads 112, and tapered end 120. In some examples, cage 100 may be fabricated, manufactured, or otherwise formed, using various types of medical grade material, including stainless steel, plastic, composite materials, or alloys (e.g., Ti-6Al-4V ELI, another medical grade titanium alloy, or other medical grade alloy) that may be corrosion resistant and biocompatible (i.e., not having a toxic or injurious effect on tissue into which it is implanted). In some examples, threads 112 may be a helical ridge wrapped around an outer surface of cage 100's shaft. In some examples, cage 100 may be cannulated having a cannulated opening 124 formed by a hollow shaft that extends from head 102 to tip 104. Cage 100 may vary in length (e.g., ranging from approximately 25 mm to 50 mm, or longer or shorter) to accommodate size and geometric variance in a joint. Other dimensions of cage 100, including major 132 and minor 133 diameters of threads 112, also may vary to accommodate size and geometric variance in a joint. In some examples, an outer surface of cage 100's shaft may taper from head 102 to tapered end 120, and thus threads 112 also may taper (i.e., be a tapered thread) from head 102 to tapered end 120 (e.g., having a range of major and minor diameters from head 102 to tapered end 120). In some examples, the tapering of threads 112, as well as tapered end 120, aids in guiding the cage through a pilot hole. In other examples, head 102 and threads 112 may be sized to fit within a tool or instrument, for example, a tissue protector 400, as described herein.

In some examples, cage 100's hollow shaft, or cannula, may be accessed (i.e., for packing material into) through an opening 124 in head 102. In some examples, head 102 may have a flat or partially flat surface (e.g., pan-shaped with rounded edge, unevenly flat, or other partly flat surface). In other examples, head 102 may have a different shape (e.g., dome, button, round, truss, mushroom, countersunk, oval, raised, bugle, cheese, fillister, flanged, or other cage head shape). In some examples, the opening in head 102 may have a receiving apparatus for a torque applying tool, such as driver. The driver may be flat head, Phillip's head, square head, hexagonal, head or any similar shape suitable to receive a tool and apply torque therefrom. In one example, the torque applying tool may be a driver having a TORX® or TORX®-like shape (i.e., six-point or six-lobed shape) (see FIG. 1D) configured to receive the tip of a TORX® or TORX®-like screwdriver (e.g., driver 902). For example, cage 100 may include head grooves 118a-118f which may start at head 102 and extend linearly into the cannula of cage 100 to receive complementary lobes on the end of a screwdriver. For a TORX® or TORX®-like opening there may be six (6) total head grooves, including, for example, head grooves 118a-118 f, to receive the complementary lobes on the tip of a TORX® or TORX®-like driver. In some examples, as shown in FIG. 1C, the opening in head 102 may be contiguous with, and form a top end of, cage 100's cannula. For example, the opening may provide access to the cannula, for example, to pack material into the cage. The opening may also include a chamfer 119 providing a lead-in for a tool into the head grooves.

As described herein, the therapeutic materials may include osteogenic compounds (e.g., bone morphogenetic protein, or other osteogenic compounds that may ossify tissue), osteoconductive materials (e.g., demineralized bone, hydroxyapatite, or other material that promotes bone growth), antibiotics, steroids, contrast materials, or other materials that may be beneficial to fusing the joint, treating inflammation or other conditions in the joint, or enabling the visualization of the area within and adjacent to the cage. For example, an osteogenic compound, such as bone morphogenetic protein or other compounds, may be packed into cage 100's cannula such that when cage 100 is inserted into a joint or traverses through a joint (e.g., a sacroiliac joint), the osteogenic compound, for example through fenestrations (e.g., fenestrations 107a-107h, 108a-108h, 109a-109h, and/or 110a-110h), may come into contact with tissue in the joint adjacent to or surrounding cage 100, and ossify the tissue to fuse the joint across and through the cage. In some examples, the osteogenic compound may enter the joint and may fill the joint, partially or entirely. In other examples, an osteoconductive material, such as demineralized bone or hydroxyapatite or other materials may be packed into cage 100's cannula. When cage 100 is inserted into a joint (e.g., the joint between ilium I and sacrum S), the osteoconductive material may come into contact with tissue in the joint adjacent to or surrounding cage 100, for example through fenestrations (e.g., fenestrations 107a-107h, 108a-108h, 109a-109h, and/or 110a-110h), and promote bone growth into the cage and the joint to fuse the joint across and through the cage. In still other examples, a substance for treating sacroilitis, such as steroids or antibiotics or other substances, may be packed into cage 100's cannula such that when cage 100 is inserted into the joint, the substance may come into contact with tissue in the joint adjacent to or surrounding cage 100, for example through fenestrations (e.g., fenestrations 107a-107h, 108a-108h, 109a-109h, and/or 110a-110h), and treat the inflamed joint tissue. In yet other examples, a contrast material may be packed into cage 100's cannula such that, when cage 100 is inserted into the joint, the contrast material within cage 100, and in some examples absorbed by tissue adjacent to or surrounding cage 100, may be viewed using visualization techniques (e.g., x-ray, fluoroscope, ultrasound, or other visualization technique). In still other examples, different materials may be packed into cage 100 for different purposes. In yet other examples, the above-described materials may also come into contact with tissue adjacent to, or surrounding, cage 100 through an opening at tip 104. As described herein, cage 100 may be packed with material prior to being inserted into the joint, and may also be packed after insertion into the joint. Also as described herein, such materials may be packed into cage 100 using a packing plunger 1102 (see, e.g., FIG. 9).

In some examples, fenestrations (e.g., fenestrations 107a-107h, 108a-108h, 109a-109h, and/or 110a-110h) may provide therapeutic openings in cage 100's shaft to enable material packed inside cage 100 to come into contact with surrounding or adjacent tissue (e.g., bone, cartilage, or other tissue in the joint) when cage 100 is implanted. Additionally or alternatively, in various examples, the fenestrations (e.g., fenestrations 107a-107h, 108a-108h, 109a-109h, and/or 110a-110h) may be shaped to provide additional cutting edges or edges suitable to clean threads formed by the tip 120. In various examples, fenestrations (e.g., fenestrations 107a-107h, 108a-108h, 109a-109h, and/or 110a-110h) are substantially circular. In other examples, the fenestrations (e.g., fenestrations 107a-107h, 108a-108h, 109a-109h, and/or 110a-110h) are oblong (e.g., substantially oval, substantially elliptical, or other suitable shapes). In other examples, fenestrations (e.g., fenestrations 107a-107h, 108a-108h, 109a-109h, and/or 110a-110h) are shaped differently (e.g., rectangular, rounded rectangular, squared, triangular, or other suitable shapes). In accordance with various embodiments and discussed herein As illustrated in FIGS. 7A and 7C, driver assembly 900 includes driver 902, mating tip 904, driver handle 906, tissue protector 404, handle 412, and tissue protector head 414. In some examples, driver 902 may be configured to drive a cage (e.g., cages 100) into a bone and/or joint. In some examples, driver 902 may have a shaft configured to fit or slide within tissue protector 404. In some examples, mating tip 904 may be shaped to engage (i.e., fit) a head of a cage (e.g., head 102). For example, driver 902 may be a TORX® driver and mating tip 904 may be shaped to fit a TORX® head cage (e.g., with a six-point or six-lobed shape). In other examples, mating tip 904 may be shaped differently to engage suitable types of cages (e.g., PHILLIPS™ (i.e., having a cruciform or cross shape with four lobes), slot, flat, Robertson, hex, or other type of cages). In some examples, driver handle 906 may be used to turn driver 902, and consequently turn a cage engaged by mating tip 904. In some examples, driver 902 may be a manual driver. In other examples, driver 902 may be powered (i.e., electrically). In some examples, driver 902 also may be ratcheting or torque-limited. In some examples, driver handle 906 may be formed separately from driver 902's shaft and driver tip 904. In some examples, handle 906 may be configured to be removably coupled with various types of drivers (e.g., TORX®, PHILLIPS™, slot, flat, Robertson, hex, or other types of cage drivers). In other examples, driver 902 and driver handle 906 may be formed differently, and are not limited to the examples shown and described. The cage 100 includes a cannula that slides over the guide wire 418 and into tissue protector sleeve 404. The driver 902 forces the cage 100 down sleeve 404 until contact is made with the bone. Then a torque is applied to cage 100 by the handle 906 causing the cage to twist into the bone.

FIG. 8A is a perspective view of a parallel guide 300 according to one embodiment being used to set another guide at a new location in a sacroiliac joint in the procedure of FIG. 3. This embodiment of the parallel guide 300 corresponds to the parallel guide illustrated in FIGS. 1A-E and discussed in more detail above.

Figure 8B:
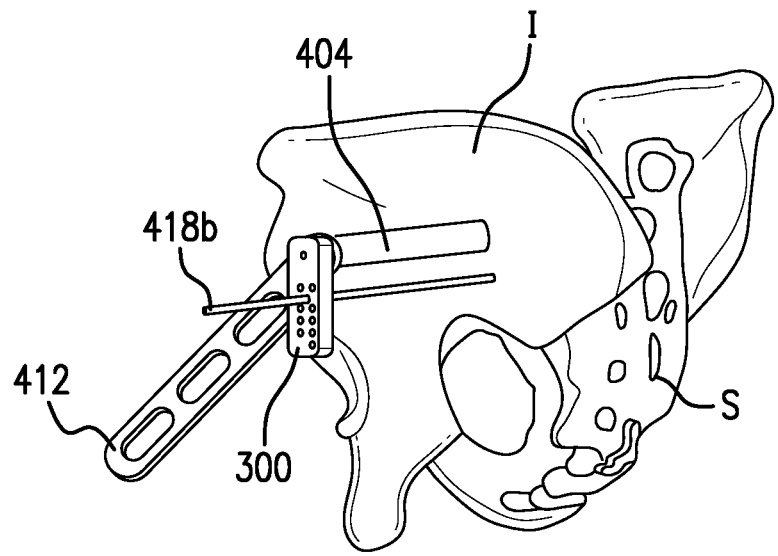
FIG. 8B is a perspective view of a parallel guide according to another embodiment being used to set a guide at a new location in a sacroiliac joint in the procedure of FIG. 3.

FIG. 8B is a perspective view of a parallel guide according to another embodiment being used to set a guide at a new location in a sacroiliac joint in the procedure of FIG. 3. This embodiment of the parallel guide 350 corresponds to the parallel guide illustrated in FIGS. 2A-F and discussed in more detail above.

Figure 9:
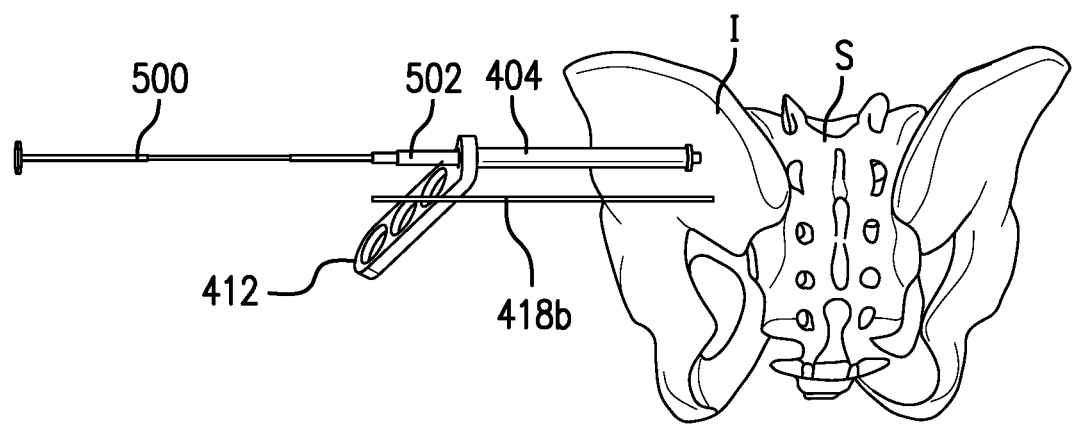
FIG. 9 illustrates a packing plunger assembly according to one embodiment placed in a tissue protector assembly for packing a cage for joint fusion in the procedure of FIG. 3.

FIG. 8A illustrates a side view of the parallel guide 300 for placement of another guide 418b. FIG. 9 illustrates a second guide 418b placed parallel to the first setup. This is accomplished by running the additional guide 418b through the spacer block as shown in FIG. 8. In some examples, guide 418 may still be in place within tissue protector 400. Once the parallel guide 300 is placed on tissue protector 400, a next guide 418b is inserted through the parallel spacer reaching down to engage the bone (e.g., an ilium).

FIG. 9 illustrates a perspective view of an exemplary packing plunger 500 placed in a dispensing tube 502. In some examples, dispensing tube 502 and plunger 500 work together to dispense therapeutic material into the cage located in the bone (e.g., ilium and/or sacrum). The plunger and the dispensing tube dispense various therapeutic materials (e.g., liquids, gases, gels, or other materials. As described herein, such therapeutic materials include osteogenic compounds (e.g., bone morphogenetic protein, or other osteogenic compounds that may ossify tissue in the joint), osteoconductive materials (e.g., demineralized bone, hydroxyapatite, or other material that promotes bone growth), antibiotics, steroids, contrast materials, or other materials that may beneficial to fusing the joint, treating inflammation or other conditions in the joint, or enabling the visualization of the area within and adjacent to the cage. In some examples, plunger 500 may be depressed to dispense material from dispensing tube 502, for example, into a cannulated cage (e.g., cages 100), which may in turn deliver said material into a joint, as described above, through the fenestrations discussed above.

Although the foregoing examples have been described in some detail for purposes of clarity of understanding, the invention is not limited to the details provided. There are many alternative ways of implementing the invention.

What is claimed is:

1. A parallel spacer for parallel spacing of a guide during surgery, comprising:
a parallel-spacer body having a top surface and a bottom surface, the parallel-spacer body defining first and second guide apertures extending through the parallel-spacer body between openings in the top and bottom surfaces and defined by internal walls; and
an external positioning protrusion extending from the bottom surface of the parallel-spacer body and ending in a lower surface, the external positioning protrusion including an orientation feature that has an internal wall defining a primary aperture sized to receive a first guide in a first orientation and hold the parallel-spacer body in a body orientation with respect to the first guide and first guide orientation, the primary aperture extending through the external positioning protrusion from the top surface to the lower surface,
wherein each of the first and second guide apertures is sized to receive and hold another guide in a parallel orientation to the first orientation, the first and second guide apertures being disposed to hold the other guide at a first and second distance, respectively, from the primary aperture, wherein the first distance is different than the second distance.

2. The parallel spacer of claim 1, wherein the primary aperture is configured to receive a pin or a wire as the first guide.

3. The parallel spacer of claim 2, wherein the pin is a guide pin.

4. The parallel spacer of claim 1, wherein a difference between the first distance and the second distance is less than a diameter of either the first or second guide apertures.

5. The parallel spacer of claim 1, wherein a difference between the first distance and the second distance is approximately the same as a diameter of the other guide.

6. The parallel spacer of claim 1, wherein a difference between the first distance and the second distance is greater than a diameter of the other guide.

7. The parallel spacer of claim 1, further comprising additional guide apertures extending between additional openings in the top surface and additional openings in the bottom surface and defined by internal walls, wherein the additional guide apertures are each sized to receive the other guide and hold the other guide in a parallel orientation to the first orientation, wherein each of the additional apertures are located at different distances from the primary aperture.

8. The parallel spacer of claim 7, wherein each of the additional guide apertures is positioned in an alternating linear pattern progressing in distance from the primary aperture, with a first set of additional guide apertures falling along a first line and a second set of the additional guide apertures falling along a second line.

9. The parallel spacer of claim 7, wherein each of the additional guide apertures all define different points that all define different lines with respect to the primary aperture defining a first point in each of the different lines.

10. The parallel spacer of claim 9, wherein each of the guide additional apertures are positioned on a curved line with respect to one another.

11. The parallel spacer of claim 1, further comprising at least two spacer markings, with a first spacer marking positioned adjacent to the first guide aperture and a second spacer marking positioned adjacent to the second guide aperture on the parallel-spacer body with each of the two spacer markings marking a first linear distance and a second linear distance.

12. The parallel spacer of claim 11, wherein the at least two spacer markings are numerical labels establishing a linear distance from a center axis of the primary aperture to a center axis of each of the respective first guide aperture and second guide aperture.

13. The parallel spacer of claim 12, wherein the parallel-spacer body is configured to allow a user to position, at a selected one of the spacer markings, a second guide such that a predetermined discrete distance relative to a previously placed guide at the primary aperture is established.

14. The parallel spacer of claim 11, wherein first linear distance and the second linear distance are fixed distances, and the at least two spacer markings indicate the respective first and second fixed distances.

15. The device of claim 1, wherein the first aperture and the second aperture are configured to receive a same size guide as the first guide.

16. The parallel spacer of claim 15, wherein the internal walls of first guide aperture, the second guide aperture, and the primary aperture have a same diameter.

17. The parallel spacer of claim 16, wherein each of the primary aperture, the first guide aperture, and the second guide aperture are cylindrical and sized to receive and position a respective one of the first guide or the other guide.

18. The parallel spacer of claim 1, wherein the external positioning protrusion is cylindrical and configured to be received into at least one of a drill guide or tissue protector.

19. The parallel spacer of claim 1, wherein the external positioning protrusion is integrally formed with the parallel-spacer body.

20. The parallel spacer of claim 1, wherein an outer surface of the external positioning protrusion is parallel with the internal wall of the first guide aperture.

21. The parallel spacer of claim 1, wherein the external positioning protrusion is configured to engage a drill guide as the first guide to maintain the other guide in a parallel orientation to an orientation of the tissue protector.

22. The parallel spacer of claim 1, wherein the external positioning protrusion includes a ridge configured to engage a tissue protector.

23. The parallel spacer of claim 1, wherein the external positioning protrusion includes a slot extending through the protrusion that allows the protrusion to flex as the protrusion is inserted into one of a tissue protector or a drill guide.

24. A parallel-spacer guide system, comprising:
the parallel spacer of claim 1; and
a tissue protector including a hollow shaft open at both ends, wherein the external positioning protrusion is configured and dimensioned for reception into the hollow shaft.

25. The parallel spacer of claim 24, wherein the external positioning protrusion has a close tolerance to the hollow shaft to maintain the other guide in a parallel orientation to an orientation of the tissue protector.

26. The parallel spacer of claim 24, wherein the tissue protector comprises a drill guide.

27. The parallel spacer of claim 1, wherein the parallel-spacer body defines third and fourth guide apertures extending through the parallel-spacer body between openings in the top and bottom surfaces and defined by internal walls, each sized to receive and hold the other guide in a parallel orientation to the first orientation, the third and fourth guide apertures being disposed at different distances from the primary aperture than the first and second distances.

28. The parallel spacer of claim 27, wherein:
the primary, first, and second apertures are each centered on a first straight line; and
the primary, third, and fourth apertures are each centered on a second straight line.

29. A parallel spacer for parallel spacing of a guide during surgery, comprising:
a parallel-spacer body having a top surface and a bottom surface, the parallel-spacer body defining first and second guide aperture extending through the parallel-spacer body between openings in the top and bottom surfaces and defined by internal walls; and
an external positioning protrusion extending from the bottom surface of the parallel-spacer body and ending in a lower surface, the external positioning protrusion including an orientation feature that has an internal wall defining a primary aperture sized to receive a first guide in a first orientation and hold the parallel-spacer body in a body orientation with respect to the first guide and first guide orientation, the primary aperture extending through the external positioning protrusion from the top surface to the lower surface, wherein each of the first and second guide apertures is sized to receive and hold another guide having a same size as the first guide in a parallel orientation to the first orientation.

* * * * *